United States Patent [19]

Nohara et al.

[11] Patent Number: 4,710,498
[45] Date of Patent: Dec. 1, 1987

[54] PYRIDYLOXY DERIVATIVES

[75] Inventors: Fujio Nohara, Takaoka; Tomoaki Fujinawa, Toyama, both of Japan

[73] Assignee: Ikeda Mohando Co., Ltd., Toyama, Japan

[21] Appl. No.: 781,881

[22] Filed: Sep. 30, 1985

[30] Foreign Application Priority Data

Oct. 2, 1984 [JP] Japan ................................. 59-206690
Mar. 12, 1985 [JP] Japan ................................... 60-50207

[51] Int. Cl.[4] ................... A61K 31/501; A61K 31/53; A61K 31/44; A61K 31/41; C07D 401/12; C07D 401/14; C07D 213/64
[52] U.S. Cl. ..................................... 514/242; 544/320; 544/321; 544/317; 544/182; 544/360; 546/193; 546/261; 546/256; 546/276; 546/277; 546/275; 546/281; 546/300; 546/255; 540/481; 540/597; 540/598; 540/601; 514/183; 514/318; 514/332; 514/333; 514/341; 514/342; 514/343; 514/351; 514/212; 514/269; 514/272; 514/273; 514/274; 514/255; 514/316; 514/340; 514/336; 514/334
[58] Field of Search ............... 546/193, 261, 255, 256, 546/276, 277, 275, 281, 300; 544/320, 321, 317, 182, 360; 514/212, 242, 269, 255, 272, 273, 274, 316, 183, 318, 332, 333, 341, 342, 343, 351, 334, 340, 336; 540/481, 597, 598, 601

[56] References Cited

U.S. PATENT DOCUMENTS

| | | | |
|---|---|---|---|
| 4,120,968 | 10/1978 | Ganellin et al. | 546/193 |
| 4,120,973 | 10/1978 | Canellin et al. | 548/336 |
| 4,166,857 | 9/1979 | Ganellin et al. | 548/204 |
| 4,440,933 | 4/1984 | Montzka | 546/193 |
| 4,466,970 | 8/1984 | Brown et al. | 546/193 |
| 4,503,051 | 3/1985 | Algieri et al. | 546/256 |
| 4,521,625 | 6/1985 | Brown et al. | 564/461 |
| 4,532,246 | 7/1985 | Ife | 514/275 |

FOREIGN PATENT DOCUMENTS

| | | |
|---|---|---|
| 0049173 | 4/1982 | European Pat. Off. . |
| 0089765 | 9/1983 | European Pat. Off. . |
| 105703 | 4/1984 | European Pat. Off. . |
| 59-84867 | 5/1984 | Japan . |
| 59-118767 | 7/1984 | Japan . |

OTHER PUBLICATIONS

Chemical Abstracts, vol. 100, No. 23, Jun. 4, 1984, pp. 585, entry 191885h.

Primary Examiner—John M. Ford

Attorney, Agent, or Firm—Oblon, Fisher, Spivak, McClelland & Maier

[57] ABSTRACT

Pyridyloxy derivatives represented by the general formula:

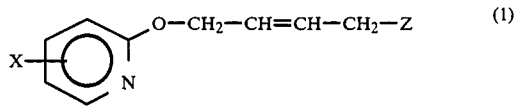

wherein the substituted group Z is either one of the following groups:

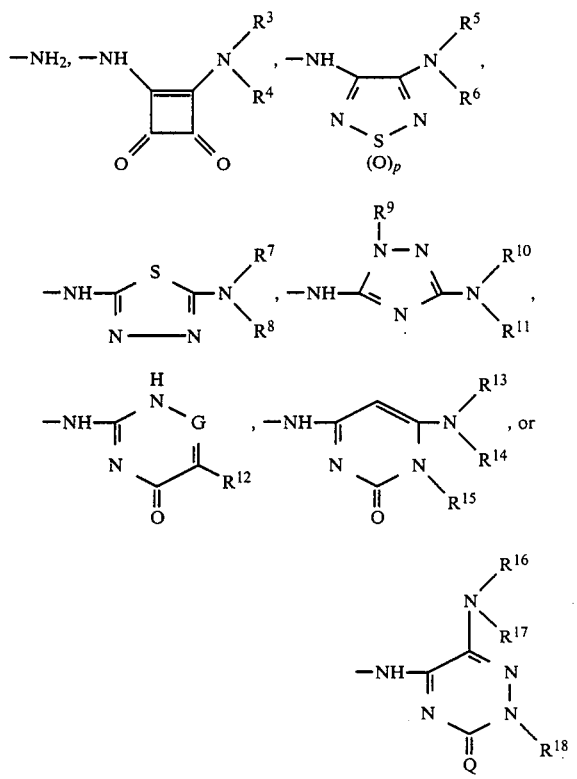

were prepared.

These derivatives exert antagonism against Histamine H2-receptors and hence are efficacious for the treatments of digestive ulcers.

22 Claims, No Drawings

PYRIDYLOXY DERIVATIVES

BACKGROUND OF THE INVENTION

The present invention relates to pyridyloxy derivatives, and more particularly to aminoalkylpyridyloxy derivatives and medically acceptable salts, hydrates and solvates thereof which exert antagonism to histamine $H_2$-receptors and thus have utility in medical treatment of digestive ulcers.

DESCRIPTION OF THE PRIOR ART

It has hitherto been well-known in the art that gastric acid secretion can be controlled by blocking the histamine $H_2$-receptors from the histamine action and that gastric secretion in an animal or a human being can be suppressed by the use of a substance having an antagonism to the histamine $H_2$-receptors. (In this connection, reference should be made to R. W. Brimblecombe et al., J. Int. Med. Res., 3, 86, 1975.)

Amongst the known histamine $H_2$-receptor antagonists, particularly well-known is Cimetidine which has been marketed as the first commercially available medicine for treating digestive ulcers.

Considerable research has been made to find substances having antagonism to histamine $H_2$-receptors which are superior to that of Cimetidine, and a variety of heterocyclic compounds were synthesized and the antagonism to histamine $H_2$-receptor thereof were investigated. Japanese Patent Laid-Open Publication Nos. 84867/1984 and 118767/1984 are pertinent references in this connection.

SUMMARY OF THE INVENTION

The object of this invention is to provide novel substituted aminoalkylpyridyloxy derivatives which exert superior antagonism to histamine $H_2$-receptors to suppress gastric secretion of animals appreciably and which also provide shielding functions to protect the mucous membrane and to promote the secretion of mucus.

The compounds provided by the present invention are aminoalkylpyridyloxy derivatives represented by the general formula:

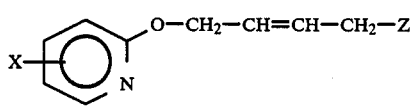

wherein X is

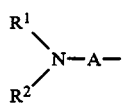

(wherein $R^1$ and $R^2$ are individually hydrogen atoms or lower alkyl groups having 1 to 6 carbon atoms, or $R^1$ and $R^2$ form, together with the bonded nitrogen atom, a four to eight-membered heterocyclic ring which may have a further substituting group or groups; A is a straight-chain or branched-chain alkylene group having 1 to 6 carbon atoms); and Z is either one of the following groups:

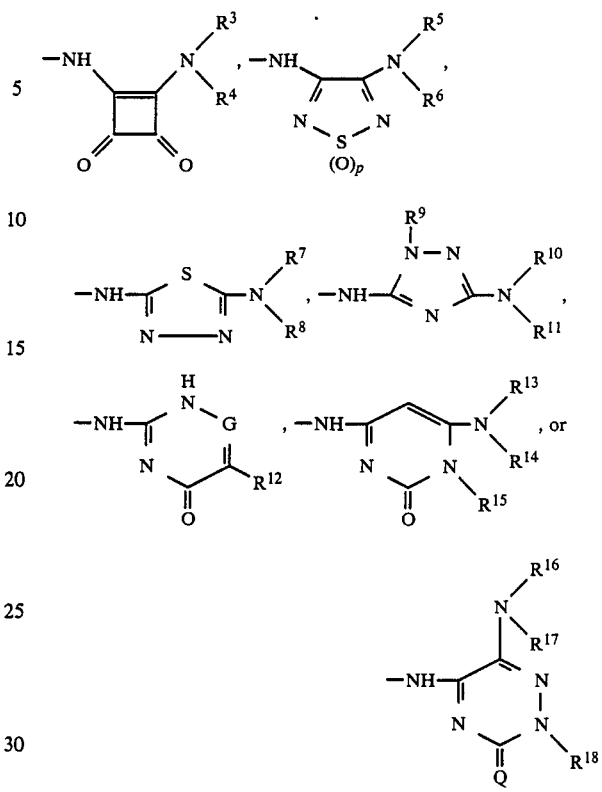

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are individually hydrogen atoms or alkyl groups having 1 to 6 carbon atoms, alkenyl, alkynyl, aralkyl, heterocyclic aryl alkyl groups; or a four to eight-membered heterocyclic group is formed respectively by $R^3$ and $R^4$, $R^5$ and $R^6$, $R^7$ and $R^8$, $R^{10}$ and $R^{11}$, $R^{13}$ and $R^{14}$, $R^{16}$ and $R^{17}$, together with the nitrogen atoms bonded therewith; $R^{12}$ is a hydrogen atom or an alkyl group having 1 to 6 carbon atoms, dialkylamino-alkyl group 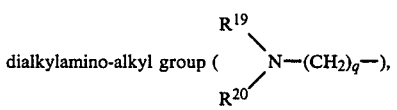

dialkylaminoalkylbenzyl group

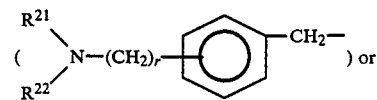

pyridylalkyl group 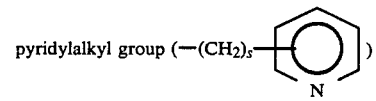

(wherein $R^{19}$, $R^{20}$, $R^{21}$ and $R^{22}$ are alkyl groups having 1 to 6 carbon atoms; q, r and s indicate integers of 1 to 6);

G is a nitrogen or carbon atom, p indicates 0, 1 or 2 and, Q indicates oxygen or sulfur; and medically acceptable salts, hydrates and solvates thereof, and pharmaceutics for digestive ulcers which comprise any of the foregoing as an effective ingredient.

DESCRIPTION OF THE PREFERRED EMBODIMENT

The present invention will now be described in detail with reference to preferred embodiments thereof.

Initially, examples of the lower alkyl group having 1 to 6 carbon atoms which are included as either one or both of the groups $R^1$ and $R^2$ are methyl, ethyl, n-propyl, iso-propyl. n-butyl, s-butyl, t-butyl, n-amyl, and n-hexyl groups.

Examples of the hetrocyclic groups formed by the combination of the groups $R^1$ and $R^2$ together with the nitrogen atom bonded therewith are azetidino-, pyrrolidino-, piperidino- and perhydroazepino-groups. These heterocyclic rings may include further substituent groups, such as hydroxyl, methoxy, ethoxy and lower alkyl groups having 1 to 6 carbon atoms.

It is preferable that a substituent X in the general formula defined in the claim should combine with pyridyne ring at the 4th or 6th position thereof.

Examples of alkylene groups, identified by A, include methylene, ethylene, propylene, iso-propylene and iso-butylene.

In the group Z contained in the general formula defined in the claim, the groups $R^3$, to $R^{22}$ include, for example, alkyl groups having 1 to 6 carbon atoms, such as methyl, ethyl, n-propyl, iso-propyl, n-butyl, sec-butyl, t-butyl, n-amyl, iso-amyl and n-hexyl; alkenyl groups, such as ethenyl, 2-propenyl, 2-butenyl and 3-butenyl; alkynyl groups, such as 2-propargyl; aralkyl groups, such as 2-dimethylaminomethylbenzyl, 3-dimethylaminomethylbenzyl, 4-dimethylaminomethylbenzyl and 3-methoxybenzyl; heterocyclic aryl alkyl groups, such as 2-pyridylmethyl, 3-pyridylmethyl, 4-pyridylmethyl, 2-furanylmethyl, 2-thiofuranylmethyl, 3-thiofuranylmethyl, 5-diemthylaminomethyl-2-furanylmethyl and 5-dimethylaminomethyl-2-thiofuranylmethyl.

Preferred heterocyclic groups, which are formed, respectively, by $R^3$ and $R^4$, $R^5$ and $R^6$, $R^7$ and $R^8$, $R^{10}$ and $R^{11}$, $R^{13}$ and $R^{14}$ and, $R^{16}$ and $R^{17}$, together with the corresponding nitrogen atoms bonded therewith, are azetidino-, pyrrolidino-, piperidino- and 4-methylpiperazino-rings.

The compounds of the invention represented by the general formula (1) can be either in the cis or trans geometrical isomer forms.

Illustrative examples of the compounds provided by the invention and represented by the general formula (1) are the following compounds including those specifically referred to in the Examples given hereinafter.

1-amino-2-[4-<4-(1-piperidinomethyl)pyridyl-2-oxy>-cis-2-butenylamino]-1-cyclonbuten-3,4-dione;
1-methylamino-2-[4-<4-(1-piperidinomethyl)pyridyl-2-oxy>-cis-2-butenylamino]-1-cyclobuten-3,4-dione;
1-[4-<4-(1-piperidinomethyl)pyridyl-2-oxy>-cis-2-butenylamino]-2-n-propylamino-1-cyclobuten-3,4-dione;
1-[4-<4-(1-piperidinomethyl)pyridyl-2-oxy>-cis-2-butenylamino]-2-propargylamino-1-cyclobuten-3,4-dione;
1-amino-2-[4-<4-(1-pyrrolidinomethyl)pyridyl-2-oxy>-cis-2-butenylamino]-1-cyclobuten-3,4-dione;
1-<4-(4-dimethylaminomethylpyridyl-2-oxy)-cis-2-butenylamino>-2-methylamino-1-cyclobuten-3,4-dione;
1-amino-2-[4-<6-(1-piperidinomethyl)pyridyl-2-oxy>-trans-2-butenylamino]-1-cyclobuten-3,4-dione;
1-methylamino-2-[4-<6-(1-piperidinomethyl)pyridyl-2-oxy>-trans-2-butenylamino]-1-cyclobuten-3,4-dione;
1-amino-2-[4-<6-(1-pyrrolidinomethyl)pyridyl-2-oxy>-trans 2-butenylamino]-1-cyclobuten-3,4-dione;
1-methylamino-2-[4-<4-(1-pyrrolidinomethyl)pyridyl-2-oxy>-trans-2-butenylamino]-1-cyclobuten-3,4-dione;
1-n-hexylamino-2-[4-<4-(1-piperidinomethyl)pyridyl-2-oxy>-cis-2-butenylamino]-1-cyclobuten-3,4-dione;
3-amino-4-[4-<4-(1-piperidinomethyl)pyridyl-2-oxy>-cis-2-butenylamino]-1,2,5-thiadiazole;
3-methylamino-4-[4-<4-(1-piperidinomethyl)pyridyl-2-oxy>-cis-2-butenylamino]-1,2,5-thiadiazole;
3-amino-4-[4-<4-(1-pyrrolidinomethyl)pyridyl-2-oxy>-cis-2-butenylamino]-1,2,5-thiadiazole;
3-methylamino-4-[4-<4-(1-pyrrolidinomethyl)pyridyl-2-oxy>-cis-2-butenylamino]-1,2,5-thiadiazole;
3-amino-4-<4-(4-dimethylaminomethylpyridyl-2-oxy)-cis-2-butenylamino>-1,2,5-thiadiazole;
3-<4-(4-dimethylaminomethylpyridyl-2-oxy)-cis-2-butenylamino>-4-methylamino-1,2,5-thiadiazole;
3-amino-4-[4-<4-(1-piperidinomethyl)pyridyl-2-oxy>-trans-2-butenylamino]-1,2,5-thiadiazole;
3-methylamino-4-[4-<4-(1-piperidinomethyl)pyridyl-2-oxy>-trans-2-butenylamino]-1,2,5-thiadiazole;
3-amino-4-<4-(4-dimethylaminomethylpyridyl-2-oxy)-trans-2-butenylamino>-1,2,5-thiadiazole;
3-<4-(4-dimethylaminomethylpyridyl-2-oxy)-trans-2-butenylamino>-4-methylamino-1,2,5-thiadiazole;
3-amino-4-[4-<4-(1-piperidinomethyl)pyridyl-2-oxy>-cis-2-butenylamino]-1,2,5-thiadiazole-1-oxide;
3-methylamino-4-[4-<4-(1-piperidinomethyl)pyridyl-2-oxy>-cis-2-butenylamino]-1,2,5-thiadiazole-1-oxide;
3-amino-4-[4-<4-(1-pyrrolidinomethyl)pyridyl-2-oxy>-cis-2-butenylamino]-1,2,5-thiadiazole-1-oxide;
3-methylamino-4-[4-<4-(1-pyrrolidinomethyl)pyridyl-2-oxy>-cis-2-butenylamino]-1,2,5-thiadiazole-1-oxide;
3-amino-4-<4-(4-dimethylaminomethylpyridyl-2-oxy)-cis-2-butenylamino>-1,2,5-thiadiazole-1-oxide;
3-amino-4-[4-<4-(1-piperidinomethyl)pyridyl-2-oxy>-trans-2-butenylamino]-1,2,5-thiadiazole-1-oxide;
3-methylamino-4-[4-<4-(1-piperidinomethyl)pyridyl-2-oxy>-trans-2-butenylamino]-1,2,5-thiadiazole-1-oxide;
3-amino-4-<4-(4-dimethylaminomethylpyridyl-2-oxy)-trans-2-butenylamino>-1,2,5-thiadiazole-1-oxide;
3-<4-(4-dimethylaminomethylpyridyl-2-oxy)-trans-2-butenylamino>-4-methylamino-1,2,5-thiadiazole-1-oxide;
3-amino-4-[4-<4-(1-piperidinomethyl)pyridyl-2-oxy>-cis-2-butenylamino]-1,2,5-thiadiazole-1,1-dioxide;
3-methylamino-4-[4-<4-(1-piperidinomethyl)pyridyl-2-oxy>-cis-2-butenylamino]-1,2,5-thiadiazole-1,1-dioxide;
3-amino-4-[4-<4-(1-pyrrolidinomethyl)pyridyl-2-oxy>-cis-2-butenylamino]-1,2,5-thiadiazole-1,1-dioxide;
3-methylamino-4-[4-<4-(1-pyrrolidinomethyl)pyridyl-2-oxy>-cis-2-butenylamino]-1,2,5-thiadiazole-1,1-dioxide;
3-amino-4-<4-(4-dimethylaminomethylpyridyl-2-oxy)-cis-2-butenylamino>-1,2,5-thiadiazole-1,1-dioxide;
3-amino-4-[4-<4-(1-piperidinomethyl)pyridyl-2-oxy>-trans-2-butenylamino]-1,2,5-thiadiazole-1,1-dioxide;
3-methylamino-4-[4-<4-(1-piperidinomethyl)pyridyl-2-oxy>-trans-2-butenylamino]-1,2,5-thiadiazole-1,1-dioxide;

3-amino-4-<4-(4-dimethylaminomethylpyridyl-2-oxy)-trans-2-butenylamino>-1,2,5-thiadiazole-1,1-dioxide;

3-<4-(4-dimethylaminomethylpyridyl-2-oxy)-trans-2-butenylamino>-4-methylamino-1,2,5-thiadiazole-1,1-dioxide;

2-amino-5-[4-<4-(1-piperidinomethyl)pyridyl-2-oxy>-cis-2-butenylamino]-1,3,4-thiadiazole;

2-methylamino-5-[4-<4-(1-piperidinomethyl)pyridyl-2-oxy>-cis-2-butenylamino]-1,3,4-thiadiazole;

2-amino-5-[4-<4-(1-pyrrolidinomethyl)pyridyl-2-oxy>-cis-2-butenylamino]-1,3,4-thiadiazole;

2-methylamino-5-[4-<4-(1-pyrrolidinomethyl)pyridyl-2-oxy>-cis-2-butenylamino]-1,3,4-thiadiazole;

2-amino-5-[4-<4-(dimethylaminomethyl)pyridyl-2-oxy<-cis-2-butenylamino]-1,3,4-thiadiazole;

2-[4-<4-(dimethylaminomethyl)pyridyl-2-oxy>-cis-2-butenylamino]-5-methylamino-1,3,4-thiadiazole;

2-amino-5-[4-<4-(1-piperidinomethyl)pyridyl-2-oxy>-trans-2-butenylamino]-1,3,4-thiadiazole;

2-methylamino-5-[4-<4-(1-piperidinomethyl)pyridyl-2-oxy>-trans-2-butenylamino]-1,3,4-thiadiazole;

2-ethylamino-5-[4-<4-(1-piperidinomethyl)pyridyl-2-oxy>-cis-2-butenylamino]-1,3,4-thiadiazole;

2-[4-<4-(1-piperidinomethyl)pyridyl-2-oxy>-cis-2-butenylamino]-5-n-propylamino-1,3,4-thiadiazole;

2-n-hexylamino-5-[4-<4-(1-piperidinomethyl)-2-oxy>-cis-2-butenylamino]-1,3,4-thiadiazole;

3-amino-1-methyl-5-[4-<4-(1-piperidinomethyl)pyridyl-2-oxy>-cis-2-butenylamino]-1H-1,2,4-triazole;

3-amino-1-methyl-5-[4-<4-(1-pyrrolidinomethyl)pyridyl-2-oxy>-cis-2-butenylamino]-1H-1,2,4-triazole;

3-amino-1-methyl-5-[4-<4-(1-piperidinomethyl)pyridyl-2-oxy>-trans-2-butenylamino]-1H-1,2,4-triazole;

3-amino-1-ethyl-5-[4-<4-(1-piperidinomethyl)pyridyl-2-oxy>-cis-2-butenylamino]-1H-1,2,4-triazole;

1-methyl-3-methylamino-5-[4-<4-(1-piperidinomethyl)pyridyl-2-oxy>-cis-2-butenylamino]-1H-1,2,4-triazole;

5-dimethylaminomethyl-2-[4-<4-(1-piperidinomethyl)pyridyl-2-oxy>-cis-2-butenylamino]-1H-pyrimidin-4-one;

5-dimethylaminomethyl-2-[4-<4-(1-pyrrolidinomethyl)pyridyl-2-oxy>-cis-2-butenylamino]-1H-pyrimidin-4-one;

5-dimethylaminomethyl-2-[4-<4-(dimethylaminomethyl)pyridyl-2-oxy>-cis-2-butenylamino]-1H-pyrimidin-4-one;

5-dimethylaminomethyl-2-[4-<4-(1-piperdinomethyl)pyridyl-2-oxy>-trans-2-butenylamino]-1H-pyrimidin-4-one;

2-[4-<4-(1-piperidinomethyl)pyridyl-2-oxy>-cis-2-butenylamino]-5-(3-pyridylmethyl)-1H-pyrimidin-4-one;

5-(3-pyridylmethyl)-2-[4-<4-(1-pyrrolidinomethyl)pyridyl-2-oxy>-cis-2-butenylamino]-1H-pyrimidin-4-one;

2-[4-<4-(dimethylaminomethyl)pyridyl-2-oxy>-cis-2-butenylamino]-5-(3-pyridylmethyl)-1H-pyrimidin-4-one;

5-(3-dimethylaminomethylbenzyl)-2-[4-<4-(1-piperidinomethyl)pyridyl-2-oxy>-cis-2-butenylamino]-1H-pyrimidin-4-one;

5-(3-dimethylaminomethylbenzyl)-2-[4-<4-(1-pyrrolidinomethyl)pyridyl-2-oxy>-cis-2-butenylamino]-1H-pyrimidin-4-one;

5-(3-dimethylaminomethylbenzyl)-2-[4-<4-(dimethylaminomethyl)pyridyl-2-oxy>-cis-2-butenylamino]-1H-pyrimidin-4-one;

5-(3-dimethylaminomethylbenzyl)-2-[4-<4-(1-piperidinomethyl)pyridyl-2-oxy>-trans-2-butenylamino]-1H-pyrimidin-4-one;

5-[5-(1,3-benzodioxolyl)methyl]-2-[4-<4-(1-piperidinomethyl)pyridyl-2-oxy>-cis-2-butenylamino]-1-pyrimidin-4-one;

3-[4-<4-(1-piperidinomethyl)pyridyl-2-oxy>-cis-2-butenylamino]-6-(3-pyridynomethyl)-1,2,4-triazin-5-one;

6-(3-pyridynomethyl)-3-[4-<4-(1-pyrrolidinomethyl)pyridyl-2-oxy>-cis-2-butenylamino]-1,2,4-triazin-5-one;

3-[4-<4-(dimethylaminomethyl)pyridyl-2-oxy>-cis-2-butenylamino]-6-(3-pyridynomethyl)1,2,4-trazin-5-one;

3-[4-<4-(1-piperidinomethyl)pyridyl-2-oxy>-trans-2-butenylamino]-6-(3-pyridynomethyl)-1,2,4-triazin-5-one;

6-(3-dimethylaminomethyl)-3-[4-<4-(1-piperidinomethyl)pyridyl-2-oxy>-cis-2-butenylamino]-1,2,4-triazin-5-one;

6-(3-dimethylaminomethyl)-3-[4-<4-(1-pyrrolidinomethyl)pyridyl-2-oxy>-cis-2-butenylamino]-1,2,4-triazin-5-one;

4-amino-6-[4-<4-(1-piperidinomethyl)pyridyl-2-oxy>-cis-2-butenylamino]-1H-pyrimidin-2-one;

4-methylamino-6-[4-<4-(1-piperidinomethyl)pyridyl-2-oxy>-cis-2-butenylamino]-1H-pyrimidin-2-one;

4-amino-6-[4-<4-(1-pyrrolidinomethyl)pyridyl-2-oxy>-cis-2-butenylamino]-1H-pyrimidin-2-one;

4-methylamino-6-[4-<-(1-pyrrolidinomethyl)pyridyl-2-oxy>-cis-2-butenylamino]-1H-pyrimidin-2-one;

4-amino-6-[4-<4-(1-piperidinomethyl)pyridyl-2-oxy>-trans-2-butenylamino]-1H-pyrimidin-2-one;

4-dimethylamino-6-[4-<4-(1-piperidinomethyl)pyridyl-2-oxy>-cis-2-butenylamino]-1H-pyrimidin-2-one;

6-amino-5-[4-<4-(1-piperidinomethyl)pyridyl-2-oxy>-cis-2-butenylamino]-1,2,4-triazin-3-one;

6-methylamino-5-[4-<4-(1-piperidinomethyl)pyridyl-2-oxy>-cis-2-butenylamino]-1,2,4-triazin-3-one;

6-amino-5-[4-<4-(dimethylaminomethyl)pyridyl-2-oxy>-cis-2-butenylamino]-1,2,4-triazin-3-one;

5-[4-<4-(1-piperidinomethyl)pyridyl-2-oxy>-cis-2-2-butenylamino]-6-propylamino-1,2,4-triazin-3-one;

6-amino-2-methyl-5-[4-<4-(1-piperidinomethyle)phridyl-2-oxy<-cis-2-butenylamino]-1,2,4-traizin-3-one;

2-butyl-6-methylamino-5-[4-<4-(1-piperidinomethyl)pyridyl-2-oxy>-trans-2-butenylamino]-1,2,4-triazin-3-one;

1-amino-2-[4-<6-(1-piperidinomethyl)pyridyl-2-oxy>-cis-2-butenylamino]-1-cyclobuten-3,4-dione;

1-methylamino-2-[4-<6-(1-piperidinomethyl)pyridyl-2-oxy>-cis-2-butenylamino]-1-cyclobuten-3,4-dione;

1-[4-<6-(1-piperidinomethyl)pyridyl-2-oxy>-cis-2-butenylamino]-2-n-propylamino-1-cyclobuten-3,4-dione;

1-[4-<6-(1-piperidinomethyl)pyridyl-2-oxy>-cis-2-butenylamino]-2-propargylamino-1-cyclobuten-3,4-dione;

1-amino-2-[4-<6-(1-pyrrolidinomethyl)pyridyl-2-oxy>-cis-2-butenylamino]-1-cyclobuten-3,4-dione;

1-methylamino-2-[4-<6-(1-pyrrolidinomethyl)pyridyl-2-oxy>-trans-2-butenylamino]-1-cyclobuten-3,4-dione;

1-amino-2-[4-<6-(1-piperidinomethyl)pyridyl-2-oxy>-trans-2-butenylamino]-1-cyclobuten-3,4-dione;

1-methylamino-2-[4-<6-(1-piperidinomethyl)pyridyl-2-oxy>-trans-2-butenylamino]-1-cyclobuten-3,4-dione;

1-amino-2-[4-<6-(1-pyrrolidinomethyl)pyridyl-2-oxy>-trans-2-butenylamino]-1-cyclobuten-3,4-dione;

1-methylamino-2-[4-<6-(1-pyrrolidinomethyl)pyridyl-2-oxy>-trans-2-butenylamino]-1-cyclobuten-3,4-dione;

1-n-hexylamino-2-[4-<6-(1-piperidinomethyl)pyridyl-2-oxy>-cis-2-butenylamino]-1-cyclobuten-3,4-dione;

3-amino-4-[4-<6-(1-piperidinomethyl)pyridyl-2-oxy>-cis-2-butenylamino]-1,2,5-thiadiazole;

3-methylamino-4-[4-<6-(piperidinomethyl)pyridyl-2-oxy>-cis-2-butenylamino]-1,2,5-thiadiazole;

3-amino-4-[4-<6-(1-pyrrolidinomethyl)pyridyl-2-oxy>-cis-2-butenylamino]-1,2,5-thiadiazole;

3-methylamino-4-[4-<6-(1-pyrrolidinomethyl)pyridyl-2-oxy>-cis-2-butenylamino]-1,2,5-thiadiazole;

3-amino-4-<4-(6-dimethylaminomethylpyridyl-2-oxy)-cis-2-butenylamino>-1,2,5-thiadiazole;

3-<4-(6-dimethylaminomethylpyridyl-2-oxy)-cis-2-butenylamino>-4-methylamino-1,2,5-thiadiazole;

3-amino-4-[4-<6-(1-piperidinomethyl)pyridyl-2-oxy>-trans-2-butenylamino]-1,2,5-thiadiazole;

3-methylamino-4-[4-<6-(1-piperidinomethyl)pyridyl-2-oxy>-trans-2-butenylamino]-1,2,5-thiadiazole;

3-amino-4-<4-(6-dimethylaminomethylpyridyl-2-oxy)-trans-2-butenylamino>-1,2,5-thiadiazole;

3-<4-(6-dimethylaminomethylpyridyl-2-oxy)-trans-2-butenylamino>-4-methylamino-1,2,5-thiadiazole;

3-amino-4-[4-<6-(1-piperidinomethyl)pyridyl-2-oxy<-cis-2-butenylamino]-1,2,5-thiadiazole-1-oxide;

3-methylamino-4-[4-<6-(1-piperidinomethyl)pyridyl-2-oxy>-cis-2-butenylamino]-1,2,5-thiadiazole-1-oxide;

3-amino-4-[4-<6-(1-pyrrolidinomethyl)pyridyl-2-oxy>-cis-2-butenylamino]-1,2,5-thiadiazole-1-oxide;

3-methylamino-4-[4-<6-(1-pyrrolidinomethyl)pyridyl-2-oxy>-cis-2-butenylamino]-1,2,5-thiadiazole-1-oxide;

3-amino-4-<4-(6-dimethylaminomethylpyridyl-2-oxy)-cis-2-butenylamino>-1,2,5-thiadiazole-1-oxide;

3-amino-4-[4-<6-(1-piperidinomethyl)pyridyl-2-oxy>-trans-2-butenylamino]-1,2,5-thiadiazole-1-oxide;

3-methylamino-4-[4-<6-(1-piperidinomethyl)pyridyl-2-oxy>-trans-2-butenylamino]-1,2,5-thiadiazole-1-oxide;

3-amino-4-<4-(6-dimethylaminomethylpyridyl-2-oxy)-trans-2-butenylamino>-1,2,5-thiadiazole-1-oxide;

3-<4-(6-dimethylaminomethylpyridyl-2-oxy)-trans-2-butenylamino>-4-methylamino-1,2,5-thiadiazole-1-oxide;

3-amino-4-[4-<6-(1-piperidinomethyl)pyridyl-2-oxy>-cis-2-butenylamino]-1,2,5-thiadiazole-1,1-dioxide;

3-amino-4-[4-<6-(1-piperidinomethyl)pyridyl-2-oxy>-cis-2-butenylamino]-1,2,5-thiadiazole-1,1-dioxide;

3-methylamino-4-[4-<6-(1-pyrrolidinomethyl)pyridyl-2-oxy>-cis-2-butenylamino]-1,2,5-thiadiazole-1,1-dioxide;

3-amino-4-<4-(6-dimethylaminomethylpyridyl-2-oxy)-cis-2-butenylamino>-1,2,5-thiadiazole-1,1-dioxide;

3-amino-4-[4-<6-(1-piperidinomethyl)pyridyl-2-oxy>-trans-2-butenylamino]-1,2,5-thiadiazole-1,1-dioxide;

3-methylamino-4-[4-<6-(1-piperidinomethyl)pyridyl-2-oxy>-trans-2-butenylamino]-1,2,5-thiadiazole-1,1-dioxide;

3-amino-4-<4-(6-dimethylaminomethylpyridyl-2-oxy)-trans-2-butenylamino>-1,2,5-thiadiazole-1,1-dioxide;

3-<4-(6-dimethylaminomethylpyridyl-2-oxy)-trans-2-butenylamino>-4-methylamino-1,2,5-thiadiazole-1,1-dioxide;

2-amino-5-[4-<6-(1-piperidinomethyl)pyridyl-2-oxy>-cis-2-butenylamino]-1,3,4-thiadiazole;

2-methylamino-5-[4-<6-(1-piperidinomethyl)pyridyl-2-oxy<-cis-2-butenylamino]-1,3,4-thiadiazole;

2-amino-5-[4-<6-(dimethylaminomethyl)pyridyl-2-oxy>-cis-2-butenylamino]-1,3,4-thiadiazole;

2-[4-<6-(dimethylaminomethyl)pyridyl-2-oxy>-cis-2-butenylamino]-5-methylamino-1,3,4-thiadiazole;

2-amino-5-[4-<6-(1-piperidinomethyl)pyridyl-2-oxy>-trans-2-butenylamino]-1,3,4-thiadiazole;

2-methylamino-5-[4-<6-(1-piperidinomethyl)pyridyl-2-oxy>-trans-2-butenylamino]-1,3,4-thiadiazole;

2-ethylamino-5-[4-<6-(1-piperidinomethyl)pyridyl-2-oxy>-cis-2-butenylamino]-1,3,4-thiadiazole;

2-[4-<6-(1-piperidinomethyl)pyridyl-2-oxy>-cis-2-butenylamino]-5-n-propylamino-1,3,4-thiadiazole;

2-n-hexylamino-5-[4-<6-(1-piperidinomethyl)pyridyl-2-oxy>-cis-2-butenylamino]-1,3,4-thaidiazole;

3-amino-1-methyl-5-[4-<6-(1-piperidinomethyl)pyridyl-2-oxy>-cis-2-butenylamino]-1H-1,2,4-triazole;

3-amino-1-methyl-5-[4-<6-(1-pyrrolidinomethyl)pyridyl-2-oxy>-cis-2-butenylamino]-1H-1,2,4-triazole;

3-amino-1-methyl-5-[4-<6-(1-piperidinomethyl)pyridyl-2-oxy>-trans-2-butenylamino]-1H-1,2,4-triazole;

3-amino-1-ethyl-5-[4-<6-(piperidinomethyl)pyridyl-2-oxy>-cis-2-butenylamino]-1H-1,2,4-triazole;

1-methyl-3-methylamino-5-[4-<6-(1-piperidinomethyl)pyridyl-2-oxy>-cis-2-butenylamino]-1H-1,2,4-traizole;

5-dimethylaminomethyl-2-[4-<6-(1-piperidinomethyl)pyridyl-2-oxy>-cis-2-butenylamino]-1H-pyrimidin-4-one;

5-dimethylaminomethyl-2-[4-<6-(1-pyrrolidinomethyl)pyridyl-2-oxy>-cis-2-butenylamino]-1H-pyrimidin-4-one;

5-dimethylaminomethyl-2-[4-<6-(dimethylaminomethyl)pyridyl-2-oxy>-cis-2-butenylamino]-1H-pyrimidin-4-one;

5-dimethylaminomethyl-2-[4-<6-(1-piperidinomethyl)pyridyl-2-oxy>-trans-2-butenylamino]-1H-pyrimidin-4-one;

2-[4-<6-(1-piperidinomethyl)pyridyl-2-oxy>-cis-2-butenylamino]-5-(3-pyridylmethyl)-1H-pyrimidin-4-one;

5-(3-pyridylmethyl)-2-[4-<6-(1-pyrrolidinomethyl)pyridyl-2-oxy>-cis-2-butenylamino]-1H-pyrimidin-4-one;

2-[4-<6-(dimethylaminomethyl)pyridyl-2-oxy>-cis-2-butenylamino]-5-(3-pyridylmethyl)-1H-pyrimidin-4-one;

5-(3-dimethylaminomethylbenzyl)-2-[4-<6-(1-piperidinomethyl)pyridyl-2-oxy>-cis-2-butenylamino]-1H-pyrimidin-4-one;

5-(3-dimethylaminomethylbenzyl)-2-[4-<6-(1-pyrrolidinomethyl)pyridyl-2-oxy>-cis-2-butenylamino]-1H-pyrimidin-4-one;

5-(3-dimethylaminomethylbenzyl)-2-[4-<6-(dimethylaminomethyl)pyridyl-2-oxy>-cis-2-butenylamino]-1H-pyrimidin-4-one;

3-[4-<6-(1-piperidinomethyl)pyridyl-2-oxy>-cis-2-butenylamino]-6-(3-pyridylmethyl)-2H-1,2,4-triazin-5-one;

6-(3-pyridylmethyl)-3-[4-<6-(1-pyrrolidinomethyl)pyridyl-2-oxy>-cis-2-butenylamino]-2H-1,2,4-triazin-5-one;

3-[4-<6-(dimethylaminomethyl)pyridyl-2-oxy>-cis-2-butenylamino]-6-(3-pyridylmethyl)-2H-1,2,4-triazin-5-one;

3-[4-<6-(1-piperidinomethyl)pyridyl-2-oxy>-trans-2-butenylamino]-6-(3-pyridylmethyl)-2H-1,2,4-triazin-5-one;

6-(3-dimethylaminomethyl)-3-[4-<6-(1-pyrrolidinomethyl)pyridyl-2-oxy>-cis-2-butenylamino]-2H-1,2,4-triazin-5-one;

4-amino-6-[4-<6-(1-piperidinomethyl)pyridyl-2-oxy>-cis-2-butenylamino]-1H-pyrimidin-2-one;

4-methylamino-6-[4-<6-(1-piperidinomethyl)pyridyl-2-oxy>-cis-2-butenylamino]-1H-pyrimidin-2-one;

4-amino-6-[4-<6-(1-pyrrolidinomethyl)pyridyl-2-oxy>-cis-2-butenylamino]-1H-pyrimidin-2-one;

6-[4-<6-(dimethylaminomethyl)pyridyl-2-oxy>-cis-2-butenylamino]-4-methylamino-1H-pyrimidin-2-one;

4-amino-6-[4-<6-(1-piperidinomethyl)pyridyl-2-oxy>-trans-2-butenylamino]-1H-pyrimidin-2-one;

4-dimethylamino-6-[4-<6-(1-piperidinomethyl)pyridyl-2-oxy>-cis-2-butenylamino]-1H-pyrimidin-2-one;

6-amino-5-[4-<6-(1-piperidinomethyl)pyridyl-2-oxy>-cis-2-butenylamino]-2H-1,2,4-triazin-3-one;

6-methylamino-5-[4-<6-(1-piperidinomethyl)pyridyl-2-oxy>-cis-2-butenylamino]-2H-1,2,4-triazin-3-one;

6-amino-5-[4-<6-(dimethylaminomethyl)pyridyl-2-oxy>-cis-2-butenylamino]-2H-1,2,4-triazin-3-one;

5-[4-<6-(1-piperidinomethyl)pyridyl-2-oxy>-cis-2-butenylamino]-6-n-propylamino-2H-1,2,4-triazin-3-one;

6-amino-2-methyl-5-[4-<6-(1-piperidinomethyl)pyridyl-2-oxy>-cis-2-butenylamino]-2H-1,2,4-triazin-3-one; and 2-butyl-6-methylamino-5-[4-<6-(1-piperidinomethyl)pyridyl-2-oxy>-trans-2-butenylamino]-2H-1,2,4-traizin-3-one.

1-[4-<4-(1-piperidinomethyl)pyridyl-2-oxy>cis-2-butenylamino]-2-(3-pyridylmethylamino)-1-cyclobuten-3,4-dione;

1-[4-<4-(1-piperidinomethyl)pyridyl-2-oxy>cis-2-butenylamino]-2-(4-pyridylmethylamino)-1-cyclobuten-3,4-dione;

1-[4-<6-(1-piperidinomethyl)pyridyl-2-oxy>-cis-2-butenylamino]-2-(3-pyridylmethylamino)-1-cyclobuten-3,4-dione;

1-[4-<6-(1-piperidinomethyl)pyridyl-2-oxy>cis-2-butenylamino]-2-(4-pyridylmethylamino)-1-cyclobuten-3,4-dione;

The compounds of the invention represented by the general furmula (1) and the salts thereof can be prepared, depending on the substituents Z included therein, through the following different processes.

(A) Compounds wherein Z is

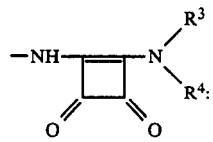

First Step:

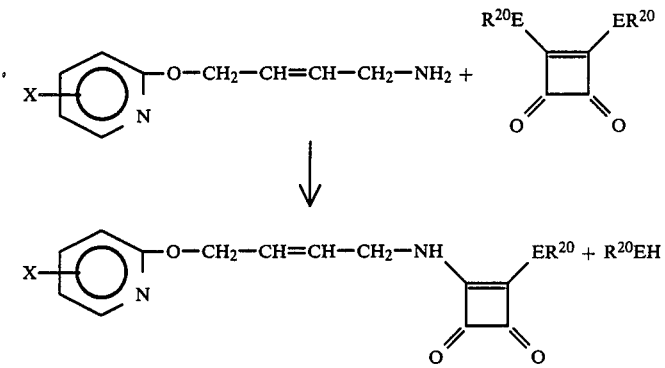

Second Step:

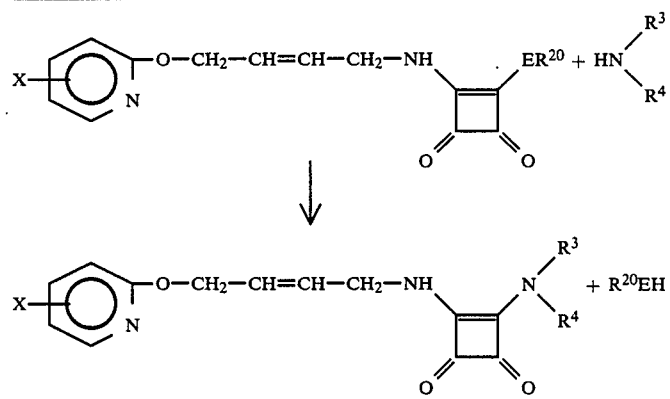

In the reaction equations set forth above, X, $R^3$ and $R^4$ are the groups as described hereinbefore and defined in the claims; $R^{20}$ is a lower alkyl, preferably methyl or ethyl; and E is —O— or —S—, preferably —O—.

The first and second steps can be carried out separately, but it is preferable that they be carried out sequentially without interruption. It is preferred that both of the starting materials be used in the equivalent molar ratio in the first step, whereas in the second step it is preferred that amine

be used in an excess amount, for example, in an amount of two to five times the moles of the resultant product of the first step.

Both steps can be carried out without using a solvent or may be carried out in an inert organic solvent such as methanol, ethanol, propanol, acetonitrile or chloroform. The reaction temperature ranges generally from $-10°$ C. to the boiling point of the solvent used, the boiling points of the usable solvents ranging generally from 50° C. to 150° C., and the preferable temperature range is from room temperature to 80° C. The time required for the completion of reaction varies depending on the reaction temperature, and both reactions can be completed within 30 minutes to 24 hours.

The pyridyloxybutenylamine derivative used in the first step is a novel compound and can be prepared, for example, by the following process:

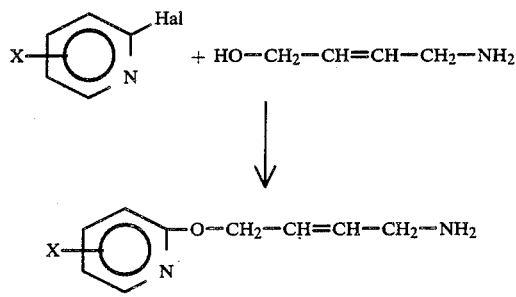

wherein X is a group as described hereinbefore and defined in the claims, Hal is a halogen atom such as chlorine, bromine, iodine and fluorine, preferably chlorine or bromine.

On the other hand, one of the compounds represented by the formula:

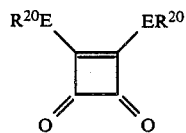

i.e. the compound

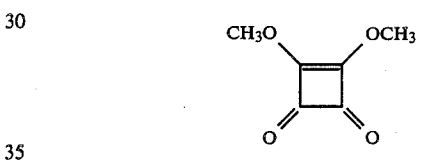

can be prepared by the process disclosed by Sidney Cohenet et al, in J. Am. Chem. Soc., 88 (7), 1533 (1966).

(B) Compounds wherein Z is

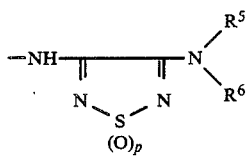

First Step:

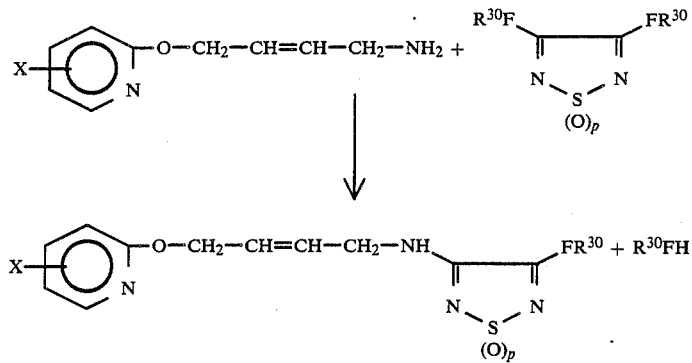

Second Step:

-continued

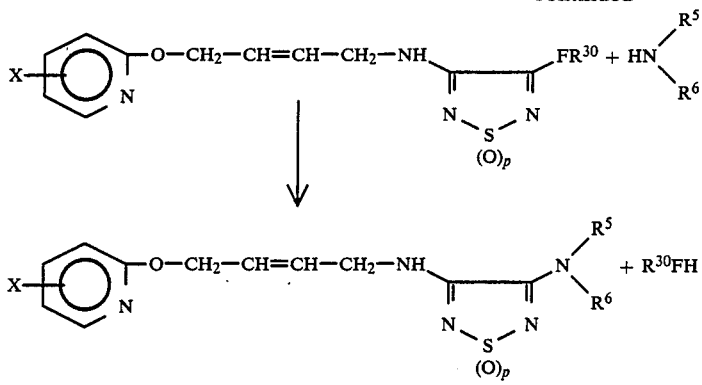 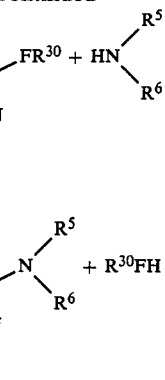

In the reaction equations set forth above, X, $R^5$ and $R^6$ are the groups as described hereinbefore and defined in the claims; $R^{30}$ is a lower alkyl, preferably methyl or ethyl; and F indicates sulfur (—S—) or oxygen (—O—).

The compounds used in the first step and represented by the formula:

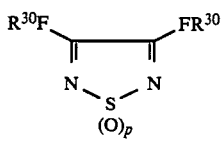

are known compounds, and 3,4-dimenthoxy-1,2,5-thiaziazole

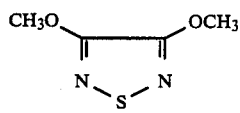

(p=0) can be prepared by a process reported by A. P. Komin et al. in J. Org. Chem., 40, 2749 (1975) or a modified process thereof, and 3,4-dimethoxy-1,2,5-thiaziazole-1-oxide

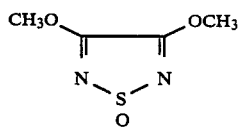

(p=1) can be prepared by a process described in Japanese Patent Laid-Open Publication No. 40675/1981 or by a modified process thereof, and 3,4-dimethoxy-1,2,5-thiaziazole-1,1-dioxide

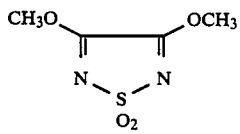

(p=2) can be prepared by a process described in R. Y. Wen et al, J. Org. Chem., 40, 2743(1975) or a modified process thereof.

The first step set forth hereinabove can be carried out, for example, by reacting one mole of a derivative of 4-<(3-dialkylaminoalkyl)pyridyl-2-oxy>-2-butenylamine with one to three moles of 3,4-dimenthoxy-1,2,5-thiadiazole, 3,4-dimethoxy-1,2,5-thiadiazole-1-oxide, or 3,4-dimethoxy-1,2,5-thiadiazole-1,1-dioxide in the absence of a solvent or in an inert organic solvent (preferably a lower alcohol such as methanol, ehtanol or propanol; or acetonitrile or chloroform) at a reaction temperature of from $-5°$ C. to $100°$ C., preferably from $0°$ C. to $30°$ C. under agitation. The reaction is completed within 30 minutes to 24 hours, and the end of the reaction may be checked by means of T.L.C. (thin layer chromatography).

The reaction of the first step may be continued into the reaction of the second step in a continuous operational sequence. Alternatively, the second step operation may be carried out after refining the resultant product of the first step, for example, by means of column chromatography.

The second step operation is carried out by dissolving the resultant product of the first step in an inert organic solvent followed by addition of an amine compound represented by the formula:

2 to 10 moles of amine, relative to one mole of the resultant product of the first step, are used; and the second step is carried out generally at a reaction temperature of from $-10°$ C. to $100°$ C., preferably from $0°$ C. to $30°$ C. The reaction is completed within 30 minutes to 24 hours.

Further, a compound represented by the formula:

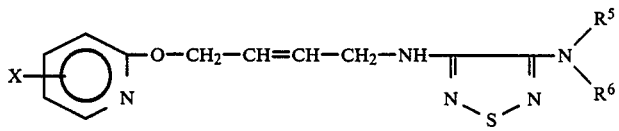

can be prepared by the following process.

The resultant product of the second step, for instance, 3-amino-4-<4-(4-dialkylaminoalkylpyridyl-2-oxy)-2-butenylamino>-1,2,5-thiaziazole-1-oxide:

N,N'-thiobisphthalimide, relative to one mole of the resultant product to convert it into 3-<4-(4-dialkylaminoalkypyridyl-2-oxy)-2-butenylamino>-4-amino-

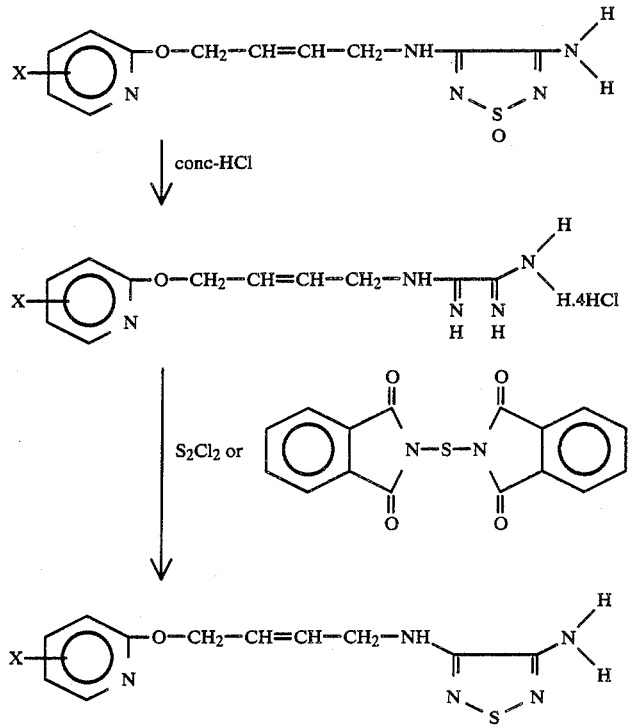

can be treated with a mineral acid (for example hydrochloric acid) to obtain tetrahydrochloride of N-4-(4-dialkylaminoalkylpyridyl-2-oxy)-2-butenyl ethanediimidamide. Thereafter, the product can be reacted with 1 to 10 moles of sulfur monochloride or 1,2,5-thiadiazole.

Aside from the aforementioned process, the same product can be prepared through the following sequential reactions:

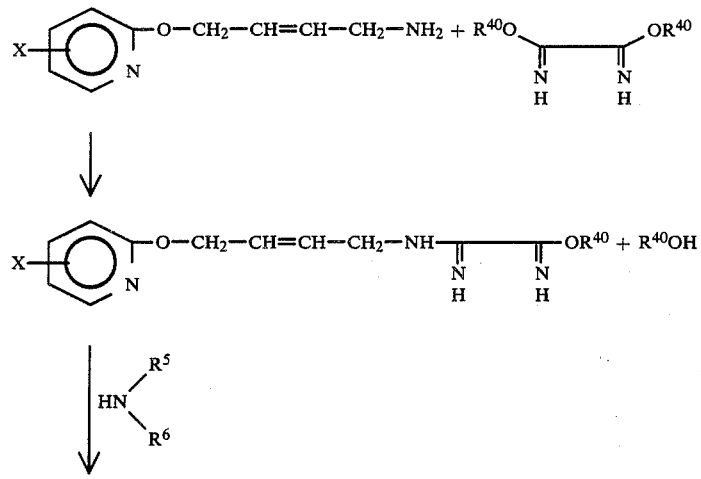

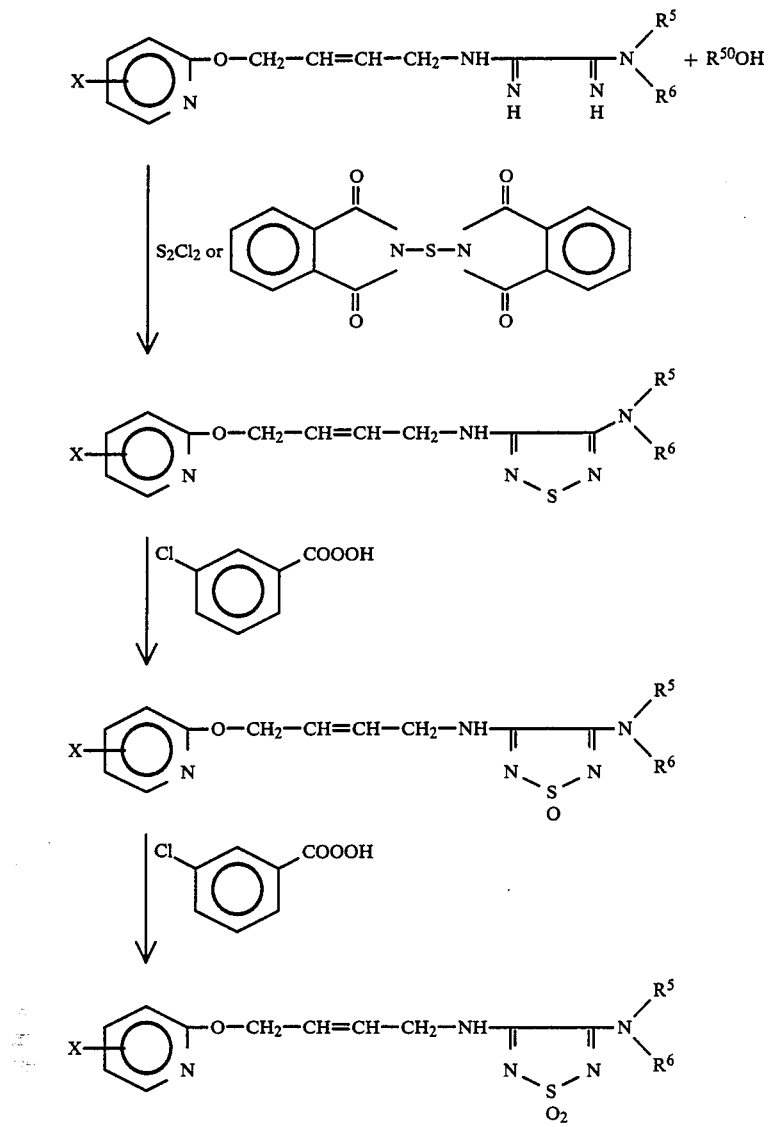
wherein X, $R^5$ and $R^6$ are the same as defined above, and $R^{40}$ indicates a lower alkyl group.
(C) Compounds wherein Z is a group represented by:
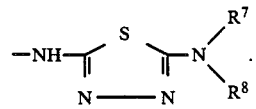
Such a compound can be prepared through the following reaction:
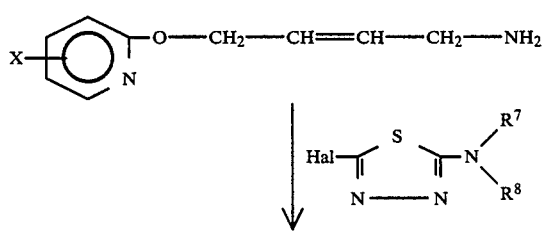

-continued

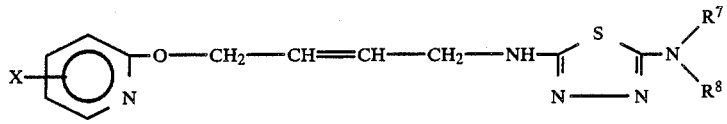

Alternatively, such a compound can be prepared by the process including the following first and second steps:

First Step:

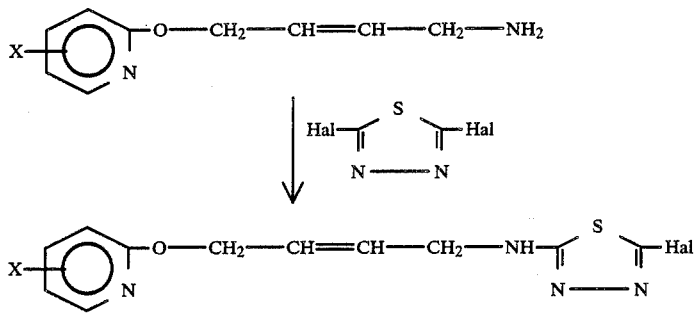

Second Step:

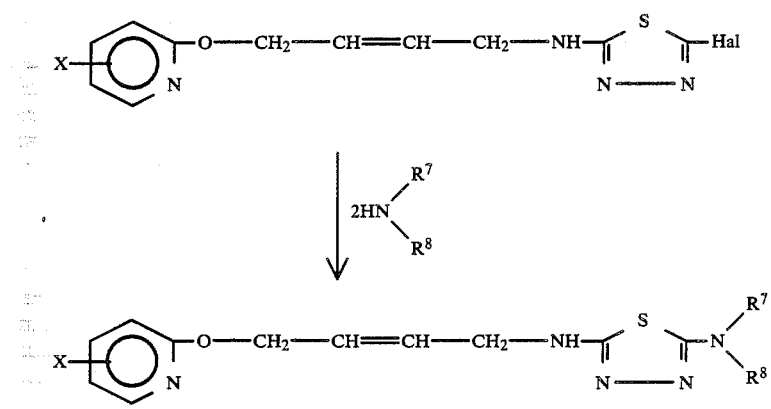

wherein X, $R^7$, $R^8$ and Hal are the same as defined above.

Although the latter process has a larger number of steps, it is generally favored because of decreased by-products and increased yield.

2,5-dihalogeno-1,3,4-thiaziazole used in the first step can be prepared by a process described in R. Stolle et al, J. Prakt. Chem., 122, 289(1929).

The first step can be carried out by reacting one mole of an amine derivative with one to three moles of 2,5-dihalogeno-1,3,4-thiaziazole in the absence of a solvent or in an inert organic solvent (preferably methanol, ethanol, propanol, DMF, DMSO) at a temperature of from 50° to 200° C.

In the second step, 2 to 10 moles of an amine compound represented by the formula:

relative to one mole of the resultant product of the first step, is used. When a low boiling point amine is used, the reaction can be carried out by heating in a bombenroll or an autoclave at a temperature of higher than the boiling point. It is suitable to use an alcohol as the solvent, and the reaction temperature ranges from 50° C. to 200° C., preferably from 70° C. to 100° C.

(D) Compounds wherein Z is

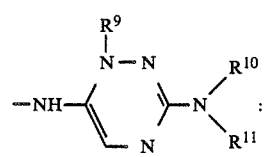

First Step:

-continued

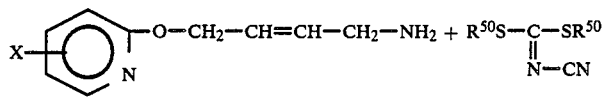

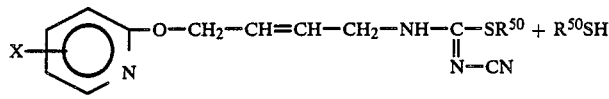

Second Step:

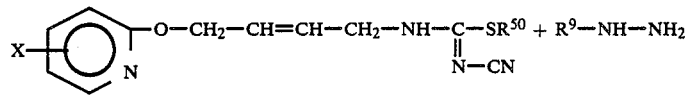

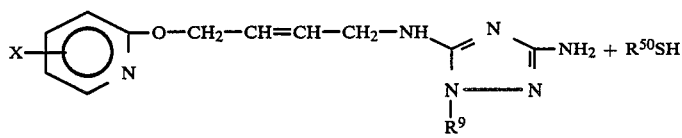

wherein X and $R^9$ are the same as defined above and $R^{50}$ is a lower alkyl, preferably methyl.

The first step is carried out by reacting starting materials in equivalent moles in the presence of an inert solvent, optionally under heating. The reaction is completed within 20 minutes to 24 hours, and it is preferred that the reaction be carried out at room temperature within 2 to 6 hours.

The second step is carried out by reacting the resultant product of the first step with a hydrazine derivative in an organic solvent such as methanol, ethanol or propanol, and the molar ratio of the hydrazine derivative to the product of the first step is in the range from 1:1 to 10:1 preferably from 1.5:1 to 3:1. The reaction is completed within 30 minutes to 24 hours at a reaction temperature of from room temperature to 150° C., and is preferably carried out at the boiling point of a lower alcohol such as methanol and ethanol within 5 to 10 hours.

Both $R^{10}$ and $R^{11}$ of the product prepared above are hydrogen atoms. Derivatives wherein $R^{10}$ and $R^{11}$ are other than hydrogen atoms can be prepared by reacting the product with a compound having an active elimination group such as haloalkyl.

N-cyanodialkyldithio-imido-carbonate used in the reaction of the first step is a known compound and can be prepared by a method described in Japanese Patent Publication No. 46-26482.

(E) Compounds wherein Z is

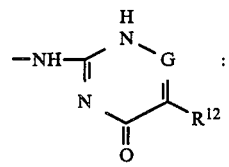

Such a compound can be prepared through the following reaction.

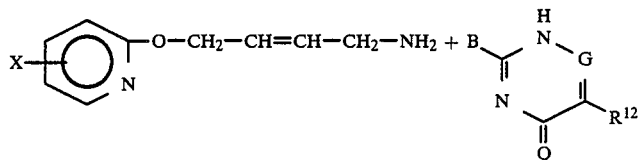

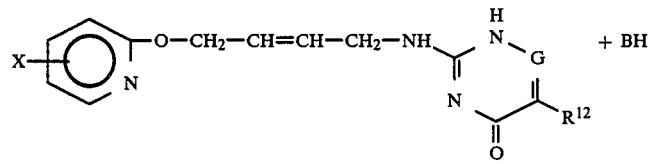

wherein X, G and $R^{12}$ are the same as refined above; and B is $R^{60}$S-($R^{60}$ is a lower alkyl, preferably methyl) or nitroamine (—NH—NO$_2$).

When B is a methylthio group, the above reaction can be carried out by melting wuthout a solvent at about 150° C. or by refluxing in pyridine.

Further, when B is nitroamine, the above reaction can be carried out by refluxing in an inert solvent such as ethanol and pyridine.

A part of the above pyrimidone derivates (G being —CH=) and triazine derivatives (G being —N=) are known compounds and can be prepared by, for example, methods described in Japanese Patent Laid-Open Publication Nos. 53-116392 and 55-11583, or by a modified mehtod thereof, which should be obvious to those skilled in the art.

(F) Compounds wherein Z in

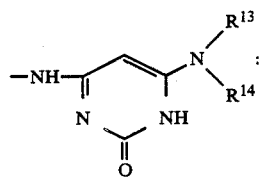

Such a compound can be prepared through the following reaction.

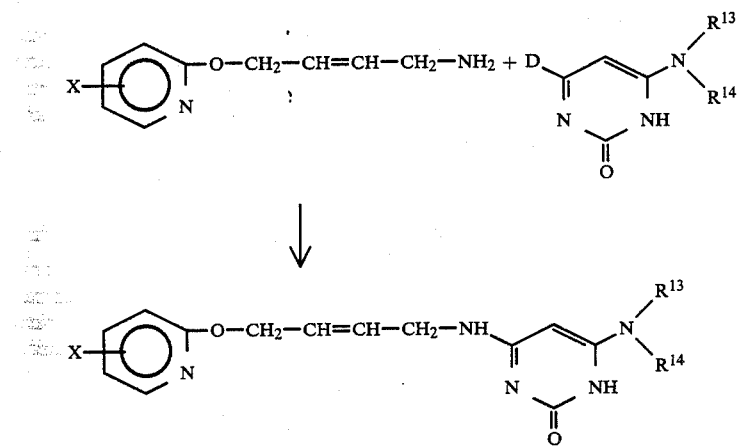

Wherein X, $R^{13}$ and $R^{14}$ are the same as defined above; and D is a halogen atom (chlorine, bromine or iodine) or a methylthio group.

The compound used in the above reaction and represented by the following formula:

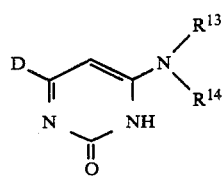

for example hydrochloride of 6-amino-4-chloro-2(1H)-pyrimidone, can be prepared by the process reported by Wolfgang Pfleiderane et al, in Ann., 657, 149 (1962). The reaction can proceed in a solvent or without using any solvent. Usable solvents include, for example, methanol, ethanol, water, DMF and DMSO. The reaction can proceed at 50° C. to 150° C. for 5 minutes to 24 hours under agitation.

(G) Compounds wherein Z is

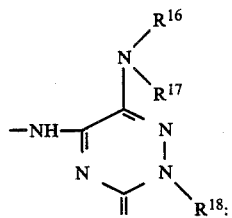

Such a compound can be prepared through the following reaction.

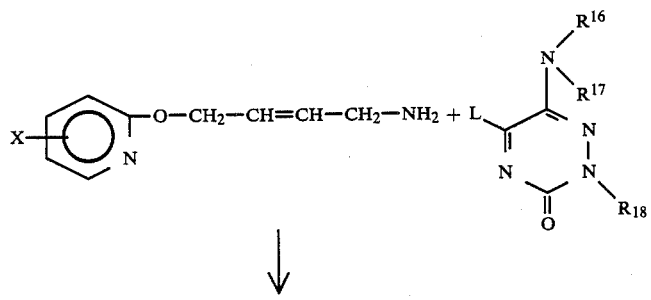

-continued

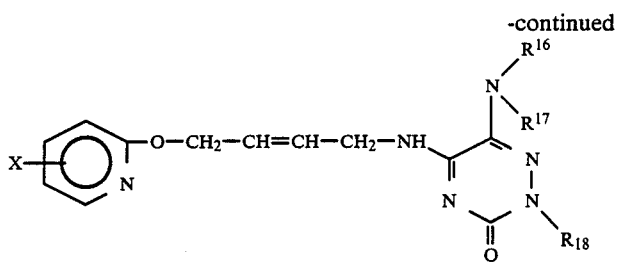

Wherein X, $R^{16}$, $R^{17}$ and $R^{18}$ are the same as defined above; and L is $R^{70}S$-($R^{70}$ is an alkyl, preferably methyl) or a hologen atom (chlorine, bromine, or iodine).

The reaction set forth above can proceed at 50° C. to 150° C. in an inert organic solvent or without using any solvent. Examples of the inert solvents include alcohols, preferably methanol, ethanol and propanol, and the reaction may proceed preferably under reflux of such a solvent.

The compounds represented by the formula:

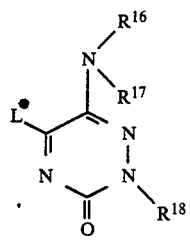

can be prepared by the process reported by C. C. Tzeng et al, in J. Org. Chem., 26, 1118 (1961), or by a modified process thereof, which should be obvious to those having ordinary skill in the art.

Pharmaceutical Efficacies of the Compounds of the Invention

Some compounds of this invention were tested and compared with Cimetidine which has been widely used for clinical applications as a medicine for digestive ulcers as having an antagonistic function on the histamine $H_2$-receptor.

(A) Inhibition Effect on Gastric Acid Secretion Induced by Histamine in Pylorus Ligated Rat The test was conducted by an improved method based on that reported by Watanabe et al., in "Pharmacometrics", Vol. 3, No. (1), pages 7 to 14 (1969).

A male Wistar rat having a body weight of about 160 g and which had not fed for 24 hours was anesthetized by an intraperitoneal dose of 1.2 g/kg of urethane. After ligating of pylorus and esophagus, the gaster anterior was incised and fitting with a double polyethylene cannula. The wall of the stomach was rinsed with 5 ml of saline at 30 minutes intervals, and the quantity of gastric acid contained in each rinsing solution was measured by titration.

The basal acid secretion was initially measured three times, and then 0.2 mg/kg of each of the compounds of this invention was administered subcutaneously and 3 mg/kg of histamine was administered subcutaneously after the lapse of an additional 30 minutes.

The quantity of gastric acid secreted after the operation was measured continuously for 3 hours. Within that measurement interval, three time points at which the increase in acid secretion reached a maximum level were selected, and the average quantity of gastric acid secreted at those time points was taken as the increase in acid secretion, which was compared with the increase in acid secretion of the control group to calculate the percent inhibition for secretion of gastric acid (Table 1).

Percent Inhibition of Gastric Acid Serection =

$$\left\{ 1 - \frac{\text{Increase in Gastric Acid Serection of Test Group}}{\text{Increase in Gastric Acid Serection of Control Group}} \right\} \times 100$$

(The result was shown as the average value of five runs.)

Each of the compounds having strong inhibition effects on the secretion of gastric acid was administered to each rat intraduodenally 30 minutes before the subcutaneous injection of histamine to find the amount to be administered for suppressing gastric acid secretion by 50% ($ED_{50}$). The results are shown in Table 2-1 and 2-2.

(B) Determination of Inhibitory Effect on Histamine $H_2$ Recepter in isolated Guinea Pig Atria A male Hartley guinea pig having a body weight of about 400 g was killed by cervical dislocation, and the atrium thereof was isolated and was suspended in an organ bath containing 50 m of a modified Ringer solution and subjected to a tension of 1 g. The number of heart beats under such condition was recorded using a polygraph.

Initially, from $1 \times 10^{-7}$ mol to $3 \times 10^{-4}$ mol of histamine was allowed to act accumulatively to depict the curve of the dosage-reaction relationship. Likewise, the curve of the dosage of histamine-reaction relationship was depicted in the presence of $5 \times 10^{-7}$ mol to $1 \times 10^{-6}$ mol of the test sample which was injected 3 minutes before. The negative logarithm ($pA_2$) of the molar concentration of the test sample required for moving the curve obtained by single administration of histamine parallel to the right side by a two-times concentration was calculated.

The results are shown in Table 1.

(C) Acute Toxicity Test

Male ddy mice each having a body weight of about 22 g and which had not eaten for 8 hours were orally dosed with the test samples, and the general symptoms and fatalities were observed from the time immediately following the administration to 14 days after the administration.

The median lethal dose ($LD_{50}$) was calculated in accordance with the Litchfield and Wilcoxon Method.

The results are shown in Table 3.

TABLE 1

Inhibitory Effect on Gastric Acid Secretion by Histamine in Pylorus ligated rat and Determination of Inhibitory Effect on Histamine $H_2$-Receptor in isolated Guinea Pig Atria

| Sample | Secretion of Gastric Acid in Rat | | Antagonistic Action against Histamine $H_2$-Receptor ($pA_2$) Determined by Using Atrium isolated from Guinea Pig |
|---|---|---|---|
| | Dosage mg/kg (SC) | Inhibition Rate (%) | |
| Compound of Ex. 1 | 0.2 | 54** | 6.47 |
| Compound of Ex. 2 | 0.2 | 60** | 6.76 |
| Compound of Ex. 3 | 0.2 | 52** | 6.33 |
| Compound of Ex. 7 | 0.2 | 90** | 6.18 |
| Compound of Ex. 8 | 0.2 | 85** | 6.31 |
| Compound of Ex. 9 | 0.2 | 62** | 6.47 |
| Compound of Ex. 10 | 0.2 | 52** | 6.74 |
| Compound of Ex. 11 | 0.2 | 101** | 6.31 |
| Compound of Ex. 12 | 0.2 | 91** | 6.58 |
| Compound of Ex. 13 | 0.2 | 84** | 6.15 |
| Compound of Ex. 15 | 0.2 | 61** | 7.45 |
| Compound of Ex. 17 | 0.2 | 69** | 6.69 |
| Compound of Ex. 19 | 0.2 | 3 | 6.12 |
| Compound of Ex. 21 | 0.2 | 65** | 6.50 |
| Compound of Ex. 22 | 0.2 | 40 | 6.44 |
| Compound of Ex. 23 | 0.2 | 36 | 5.81 |
| Compound of Ex. 25 | 0.2 | 55* | 6.77 |
| Compound of Ex. 26 | 0.2 | 83** | 6.58 |
| Compound of Ex. 27 | 0.2 | 88** | 6.56 |
| Compound of Ex. 29 | 0.2 | 74** | 6.15 |
| Compound of Ex. 32 | 0.2 | 33 | 6.31 |
| Compound of Ex. 33 | 0.2 | 34 | 6.18 |
| Compound of Ex. 34 | 0.2 | 81** | 6.03 |
| Compound of Ex. 35 | 0.2 | 74** | 5.96 |
| Compound of Ex. 36 | 0.2 | 72** | 6.58 |
| Compound of Ex. 39 | 0.2 | 36 | 5.81 |
| Compound of Ex. 41 | 0.2 | 32 | 5.72 |
| Compound of Ex. 43 | 0.2 | 44* | 6.21 |
| Compound of Ex. 45 | 0.2 | 36 | — |
| Compound of Ex. 47 | 0.2 | 40* | — |
| Compound of Ex. 49 | 0.2 | 45* | 5.77 |
| Control (Cimetidine) | 2.0 | 72** | 6.26 |

Note:
Values affixed with * and ** indicate that significant differences as of $P < 0.05$ and $P < 0.01$ were observed as compared to the control group.

TABLE 2

Inhibitory Effect of intraduodenally administered compounds of the invention on Gastric Acid Secretion induced by Histamine in Rat

| Sample | Median effective dose ($ED_{50}$) inhibiting Gastric Acid Section (mg/kg) (95% Reliability Limit) | Efficacy Ratio relative to Cimetidine (Cimetidine = 1) |
|---|---|---|
| Compound of Ex. | | |
| 1. | 0.15 (0.03~0.89) | 46.6 |
| 2. | 0.27 (0.04~1.65) | 25.9 |
| 4. | 0.11 (unmeasurable) | 63.6 |
| 7. | 0.44 (0.06~3.48) | 15.9 |
| 9. | 0.46 (0.07~2.97) | 15.2 |
| 13. | 0.50 (0.09~2.94) | 14.0 |
| 15. | 0.38 (0.07~2.2) | 18.4 |
| 17. | 0.14 (unmeasurable) | 50.0 |
| 25. | 0.14 (unmeasurable) | 50.0 |
| 30. | 0.26 (unmeasurable) | 26.9 |
| 31. | 0.28 (unmeasurable) | 25.0 |
| Control (Cimetidine) | 7.0 (1.79~27.3) | 1 |
| Compound of Ex. | 0.25 (0.06~3.48) | 32.8 |
| 32 | 0.25 (0.06~3.48) | 32.8 |
| 36 | 0.2 (unmeasurable) | 41.0 |
| Control (Cimetidine) | 8.2 (2.87~28.37) | 1 |

TABLE 3

Acute Toxicity Test on Mice Dosed Orally

| Sample | Median lethal dose ($LD_{50}$) mg/kg P.O. |
|---|---|
| Compound of Ex. 1 | >1500 |
| Compound of Ex. 2 | >1500 |
| Compound of Ex. 9 | >1500 |
| Compound of Ex. 11 | >1500 |
| Compound of Ex. 12 | >1500 |
| Compound of Ex. 19 | >1500 |
| Compound of Ex. 22 | 1600 |
| Compound of Ex. 27 | >1500 |
| Compound of Ex. 29 | 1250 |
| Control (Cimetidine) | 3300 |

As will be clearly seen from Table 1, the inhibitive actions of the respective compounds, prepared by Examples of the invention and administered subcutaneously on gastric acid secretion induced by histamine were greater than that of Cimetidine. The antagonistic actions against Histamine $H_2$-receptor of the compounds of this invention were comparable with or superior to that of Cimetidine, when tested using isolated right atria of guinea pigs. Particularly, the antagonistic actions of the compound of example 15 were strong.

Another characteristic effect of the compound of this invention that was ascertained is that the inhibitory effect on gastric acid secretion by the intraduodenal administration, which is similar to oral administration, was extremely high. For instance, as shown in Tables 2-1, and 2-2, from their $ED_{50}$ values, the compounds prepared, respectively, by Examples 1, 2, 4, 17, 25, 30, 31, 32 and 36 were about 46.6, 25.9, 63.6, 50.0, 50.0, 26.9, 25.0, 32.8 and 41.0 times more effective than the $ED_{50}$ value of Cimetidine.

The acute toxicity tests conducted by administering the compounds to mice orally revealed that the compounds of examples 22 and 29 had lower $LD_{50}$ values than that of Cimetidine.

Other tested compounds had the $LD_{50}$ values of more than 1500 mg/kg, showing that the toxicities thereof were low.

Accordingly, it should be appreciated that the compounds of this invention have remarkable utility when used as anti-pectic ulcer drugs, since they exhibit powerful inhibitory effects against Histamine $H_2$-receptor and potent suppression effects on gastric acid secretion and yet are less toxic.

The compounds of this invention may be used either in the free form or in the form of acid addition salts thereof. Pharmaceutically acceptable acid addition salts of the compounds of this invention are, for example, inorganic acid addition salts such as hydrochloride, hydrobromide, sulfate, nitrate and organic acid addition salts such as acetate, propionate, citrate, malate, fumarate, methanesulfonate and so forth.

EXAMPLES OF THE INVENTION

Example 1

Preparation of
1-amino-2-[4-<4-(1-piperidinomethyl)pyridyl-2-oxy>-cis-2-butenylamino]-1-cyclobuten-3,4-dione (A)
4-<4-(1-piperidinomethyl)pyridyl-2-oxy>-cis-2-butenylamine 12 grams of 60% sodium hydride was dispersed in 481 ml of absolute tetrahydrofuran, and slowly added with 24 g (0.276 mol) of 4-amino-cis-2-buten-1-ol. The reaction solution was stirred at 50° C. for 30 minutes followed by cooling, and then slowly added with 44 g (0.173 mol) of 2-bromo-4-(1-piperidinomethyl)pyridine (prepared by applying the method described in Japanese Patent Laid-Open Publication No. 58-170779) in 40 ml of tetrahydrofuran and the resultant mixture was refluxed and stirred for 40 hours. The solvent was distilled off after the completion of the reaction, and the residue was added with 200 ml of water and extracted with 200 ml of dichloromethane four times. The solvent was distilled off after drying an organic solvent layer with magnesium sulfate anhydrous, and the residue was passed through a silica gel chromatograph column for purification, followed by elution with a mixed solution of methanol-ethyl acetate (1:4). As a result, 38.7 g (85.9%) of the captioned compound was obtained as a light brown oily product.

IR(neat, cm$^{-1}$): 3400, 3300, 2950, 1620, 1563, 1480, 1420, 1315, 1040, 830.

NMR(CDCl$_3$, ppm): 1.2–1.9 (6H, m), 2.1–2.6 (4H, m), 2.9 (2H, s), 3.2–3.7 (4H, m), 4.7–5.0 (2H, d), 5.6–5.9 (2H, t), 6.65 (1H, s), 6.7–6.9 (1H, d), 7.9–8.1 (1H, d).

(B)

1-methoxy-2-[4-<4-(1-piperidinomethyl)pyridyl-2-oxy>-cis-2-butenylamino]-1-cyclobuten-3,4-dione 1.42 grams (0.01 mol) of dimethyl squalate (prepared by the process reported by Sideny Cohen et al, in J. Amer. Chem. Soc., Vol 88, 1533 (1966)) was dissolved in 50 ml of absolute methanol and cooled at 5° C. Then a solution of 2.61 grams (0.01 mol) of 4-<4-(1-piperidinomethyl)pyridyl-2-oxy>-cis-2-butenylamine which was prepared by the method described in example 1-(A) in 20 ml of absolute methanol was dropped into the dimethyl squalate solution obtained above at 5° C. of solution temperature, with stirring, and was stirred at room temperature for an additional 6 hours. The solvent was distilled off under reduced pressure after the completion of the reaction, and the residue was passed through a silica gel chromatograph column to purify the same, followed by elution with a mixed solution of ethyl acetate:methanol=4:1. As a result, 3.4 g (Yield: 91.6%) of the captioned compound was obtained as a light yellow oily product.

IR(neat, cm$^{-1}$): 3250, 2950, 1810, 1720, 1620, 1405, 1040, 1000, 925, 830, 785.

NMR(CDCl$_3$, ppm): 1.1–1.8 (6H, m), 2.1–2.6 (4H, m), 3.35 (2H, s), 4.0–4.5 (2H, m), 4.3 (3H, s), 4.7–5.0 (2H, d), 4.9–5.5 (2H, m), 6.6 (1H, s), 6.7–6.9 (1H, d), 7.8–8.2 (1H, d).

(C)

1-amino-2-[4-<4-(1-piperidinomethyl)pyridyl-2-oxy>-cis-2-butenylamino]-1-cyclobuten-3,4-dione 1.2 grams (3.2 m mol) of 1-methoxy-2-[4-<4-(1-piperidinomethyl)pyridyl-2-oxy>-cis-2-butenylamino]-1-cyclobuten-3,4-dione obtained in example 1-(B) was dissolved in 25 ml of absolute methanol to obtain a solution through which dry ammonia gas was passed at 5° C. of reaction temperature for 20 minutes, and then the solution was stirred at room temperature for an additional 2 hours.

The solvent was distilled off under reduced pressure after the completion of the reaction, and the residue was passed through a silica gel chromatograph column to purify the same, followed by elution with a mixed solution of ethyl acetate and methanol (4:1) and recrystallization from methanol. As a result, 0.75 g (Yield: 65.2%) of the captioned compound was obtained as a colorless crystal having a melting point of 225° to 230° C., at which temperature it decomposed.

IR(KBr, cm$^{-1}$): 3110, 2950, 1810, 1650, 1550, 1435, 1400, 1360, 1150, 1030, 640.

NMR(CDCl$_3$, ppm): 1.2–1.8 (6H, m), 2.1–2.6 (4H, m), 3.3 (2H, s), 4.1–4.5 (2H, m), 4.8–5.1 (2H, d), 5.5–5.9 (2H, m), 6.6 (1H, s), 6.7–6.9 (1H, d), 7.0–7.5 (2H, m, Eliminated by the D$_2$O treatment), 7.8–8.1 (1H, d).

Example 2

Preparation of 1-methylamino-2-[4-<4-(1-piperidinomethyl)pyridyl-2-oxy>-cis-2-butenylamino]-1-cyclobuten-3,4-dione

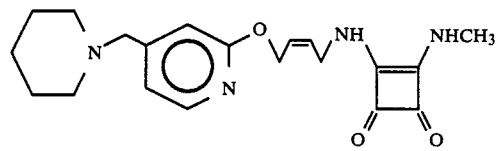

Yield: 54.3%.

Melting Point: 207° to 210° C. (d).

IR(KBr, cm$^{-1}$): 3200, 2950, 1805, 1640, 1570, 1400, 1290, 1160, 1040, 835, 740, 600.

NMR(DMSO-d$_6$/CDCl$_3$, ppm): 1.2–1.9 (6H, m), 2.1–2.7 (4H, m), 3.15 (3H, s), 3.35 (2H, s), 4.1–4.6 (2H, m), 4.7–5.1 (2H, m), 5.5–6.0 (2H, m), 6.65 (1H, s), 6.7–6.9 (1H, d), 7.0–7.6 (1H, m, Eliminated by the treatment with D$_2$O), 7.9–8.3 (1H, d).

Example 3

Preparation of 1-amino-2-<4-(6-dimethylaminomethyl-pyridyl-2-oxy)-cis-2-butenylamino>-1-cyclobuten-3,4-dione (A)

4-(4-dimethylaminomethylpyridyl-2-oxy)-cis-2-butenylamine

In accordance with the procedure of example 1-(A) but using 37.2 grams (0.173 mol) of 2-bromo-4-dimethylaminomethylpyridine in place of 44 grams of 2-bromo-4-(1-piperidinomethyl)pyridine, there was obtained 27.1 g (Yield: 74.2%) of the captioned compound as a light brown oily product.

IR(neat, cm$^{-1}$): 3400, 3200, 2950, 2800, 1660, 1620, 1560, 1410, 1290, 1155, 1020, 820.

NMR(CDCl$_3$, ppm): 2.05 (2H s, Eliminated by the D$_2$O treatment), 2.2 (6H, s), 3.2–3.7 (4H, m), 4.7–5.1 (2H, d), 5.5–6.0 (2H, t), 6.6 (1H, s), 6.7–6.9 (1H, d), 7.9–8.2 (2H, d).

(B)

1-methoxy-2-<4-(4-dimethylaminomethylpyridyl-2-oxy)-cis-2-butenylamino>-1-cyclobuten-3,4-dione In accordance with the procedure of example 1-(B) but using 2.11 g (0.01 m mol) of 4-(4-dimethylaminomethylpyridyl-2-oxy)-cis-2-butenylamine in place of 4-<4-(1-piperidinomethyl)pyridyl-2-oxy>-cis-2-butenylamine, there was obtained 2.6 g (Yield: 78.5%) of the captioned compound as a light yellow oily product.

IR(neat, cm$^{-1}$): 3250, 2960, 1810, 1715, 1610, 1400, 1315, 1160, 1035, 830, 605.

NMR(CDCl₃, ppm): 2.25 (6H, s), 3.7–4.2 (2H, m), 4.3 (3H, s), 4.7–5.0 (2H, d), 5.4–6.0 (2H, m), 6.6 (1H, s), 6.7–6.9 (1H, d), 7.8–8.2 (1H, d).

(C)

1-amino-2-<4-(4-dimethylaminomethylpyridyl-2-oxy)-cis-2-butenylamino>-1-cyclobuten-3,4-dione In accordance with the procedure of example 1-(C) but using 1.06 g (3.2 m mol) of 1 -methoxy-2-<4-(4-dimethylaminomethylpyridyl-2-oxy)-cis-2-butenylamino>-1-cyclobuten-3,4-dione in place of 1-methoxy-2-[4-<4-(1-piperidinomethyl)pyridyl-2-oxy>-cis-2-butenylamino]-1-cyclobuten-3,4-dione, there was obtained 0.71 g (Yield: 70.2%) of the captioned compound in a light yellow crystal form. The melting point of the crystal obtained by additional recrystallization from methanol was 222° to 224° C., at which the crystal decomposed.

IR(KBr, cm⁻¹): 3320, 3150, 1810, 1640, 1570, 1310, 1150, 1020, 820, 690, 600.

NMR(DMSO-d₆, ppm): 2.3 (6H, s), 3.0 (1H, s, Eliminated by the D₂O treatment), 3.35 (2H, s), 4.1–4.5 (2H, m), 4.8–5.1 (2H, d), 5.6–6.0 (2H, m), 6.75 (1H, s), 6.9–7.05 (1H, d), 7.3–7.8 (2H, m, Eliminated bu the D₂O treatment), 8.0–8.2 (1H, d).

Example 4

Preparation of 1-methylamino-2-<4-(4-dimethylaminomethylpyridyl-2-oxy)-cis-2-butenylamino>-1-cyclobuten-3,4-dione

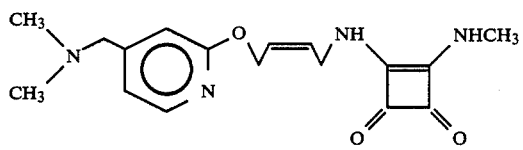

Yield: 36.2%.
Melting Point: 195° to 202° C. (Recrystallized from methanol) IR(KBr, cm⁻¹): 3200, 2950, 2800, 1810, 1660, 1570, 1400, 1310, 1290, 1150, 1030, 970, 820, 600

NMR(DMSO-d₆, ppm): 2.35 (6H, s), 3.1–3.4 (3H, m), 3.55 (2H, s), 4.8–5.0 (2H, d), 5.5–5.9 (2H, m), 5.8–6.2 (1H, m, Eliminated by the treatment with D₂O), 6.67 (1H, s), 6.7–6.9 (1H, d), 7.6–7.9 (1H, m, Eliminated by the treatment with D₂O), 7.9–8.1 (1H, d).

Example 5

Preparation of 1-<4-(4-dimethylaminomethylpyridyl-2-oxy)-cis-2-butenylamino>-2-n-hexylamino-1-cyclobuten-3,4-dione

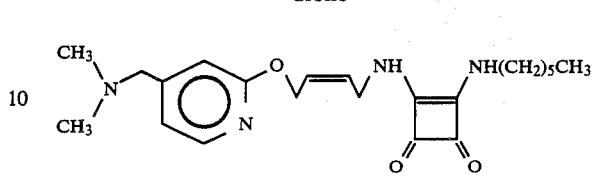

Yield: 24.2%.
Melting Point: 120° to 122° C. (Recrystallized from methanolhexane).

IR(KBr, cm⁻¹): 3200, 2950, 1810, 1650, 1580, 1430, 1310, 1150, 1030, 820, 740, 600.

NMR(CDCl₃, ppm): 0.6–1.9 (11H, m), 2.2 (6H, s), 2.3–2.6 (1H, m, Eliminated by the treatment with D₂O), 2.35 (2H, s), 3.4–3.8 (2H, m), 4.3–4.7 (2H, m), 4.8–5.1 (2H, d), 5.7–6.0 (2H, m), 6.67 (1H, s), 6.7–6.9 (1H, d), 6.6–7.0 (1H, m, Eliminated by the treatment with D₂O), 7.1–8.1 (1H, d)

Example 6

Preparation of 1-<4-(4-dimethylaminomethylpyridyl-2-oxy)-cis-2-butenylamino>-2-(2-propargylamino)-1-cyclobuten-3,4-dione

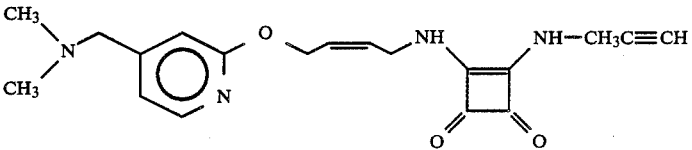

Yield: 57.4%.
Melting Point: 153° to 155° C. (Recrystallized from methanol).

IR(KBr, cm⁻¹): 3200, 2900, 2800, 1810, 1160, 1570, 1480, 1420, 1350, 1290, 1140, 1100, 1020, 920, 820, 730, 640.

NMR(DMSO-d₆, ppm): 2.25 (6H, s), 3.35 (2H, s), 4.2–4.6 (4H, m), 4.8–5.1 (2H, d), 5.6–6.0 (2H, m), 6.67 (1H, s), 6.7–6.95 (1H, d), 7.0–7.6 (2H, b, Eliminated by the treatment with D₂O), 7.9–8.1 (1H, d).

Example 7

Preparation of 3-amino-4-[4-<4-(1-piperidinomethyl)pyridyl-2-oxy>-cis-2-butenylamino]-1,2,5-thiadiazole-1-oxide (A)

3-ethoxy-4-[4-<4-(1-piperidinomethyl)pyridyl-2-oxy>-cis-2-butenylamino]-1,2,5-thiadiazole-1-oxide 2.61 grams (0.01 mol) of 4-<4-(1-piperidinomethyl)-pyridyl-2-oxy>-cis-2-butenylamine (obtained by example 1-(A)) was dissolved in 50 ml of absolute ethanol and added with 1.90 g (0.01 mol) of 3,4-diethoxy-1,2,5-thiadiazole-1-oxide (prepared by applying the method described in Japanese Patent Laid-Open Publication No. 56-40675) followed by agitation at room temperature for 2 hours. The solvent was distilled off under reduced pressure after the completion of the reaction, and the residue was passed through a silica gel chromatograph column to purify the same, followed by elution with a mixed solution of ethyl acetate:methanol=4:1. As a result, 3.34 g (Yield: 82.5%) of the captioned compound was obtained as a colorless oily product.

IR(neat, cm⁻¹): 3300, 3000, 1620, 1575, 1440, 1330, 1270, 1130, 1040, 850, 800, 730, 635.

NMR(CDCl₃, ppm): 1.2–1.9 (9H, m), 2.1–2.7 (4H, m), 3.4 (2H, s), 3.8–4.3 (2H, m), 4.3–4.7 (2H, q), 4.8–5.1 (2H, d), 5.5–6.0 (2H, m), 6.7 (1H, s), 6.7–7.0 1H, d), 7.8–8.2 (1H, d)

(B)
3-amino-4-[4-<4-(1-piperidinomethyl)pyridyl-2-oxy>-cis-2-butenylamino]-1,2,5-thiadiazole-1-oxide 2.03 g (5 m mol) of 3-ethoxy-4-[4-<4-(1-piperidinomethyl)pyridyl-2-oxy>-cis-2-butenylamino]-1,2,5-thiadiazole-1-oxide was dissolved in 40 ml of absolute ethanol, added with 2 ml of ethanol solution saturated with ammonia gas, and agitated at room temperature for 30 minutes. The solvent was distilled off under reduced pressure after the completion of the reaction, and the residue was passed through a silica gel chromatograph column to purify the same, followed by elution with a mixed solution of ethyl acetate:methanol=4:1. As a result, 1.37 g (Yield: 72.9%) of the captioned compound was obtained in a colorless crystal form. The melting point of the crystal obtained was 173° to 176° C.

IR(KBr, cm⁻¹): 3330, 2950, 2800, 1615, 1580, 1480, 1420, 1350, 1300, 1150, 1040, 820, 620.

NMR(DMSO-d₆/CDCl₃, ppm): 1.1–1.8 (6H, m), 2.05–2.65 (4H, m), 3.3 (2H, s), 3.8–4.3 (2H, d), 4.6–5.1 (2H, d), 5.5–6.0 (2H, m), 6.67 (1H, s), 6.7–7.0 (1H, d), 7.25–8.25 (3H, m, 2H were eliminated by the D₂O treatment.)

Example 8

Preparation of 3-methylamino-4-[4-<4-(1-piperidinomethyl)pyridyl-2-oxy>-cis-2-butenylamino]-1,2,5-thiadiazole-1-oxide

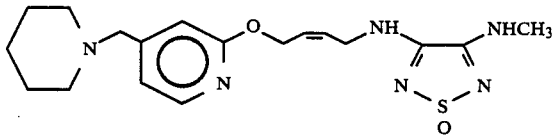

Yield: 70.7%.
Melting Point: 87° to 90° C.

IR(KBr, cm⁻¹): 3300, 3120, 2930, 1610, 1570, 1405, 1300, 1150, 1030, 835, 615.

NMR(DMSO-d₆, ppm): 1.1–1.8 (6H, m), 2.05–2.6 (4H, m), 2.9 (2H, s), 3.4 (2H, s), 3.8–4.3 (2H, m), 4.65–5.0 (2H, d), 5.4–5.9 (2H, m), 6.6 (1H, s), 6.7–6.9 (1H, d), 7.5–8.1 (1H, d).

Example 9

Preparation of 3-amino-4-[4-<4-(1-piperidinomethyl)pyridyl-2-oxy>-trans-2-butenylamino]-1,2,5-thiadiazole-1-oxide (A)
4-<4-(1-piperidinomethyl)pyridyl-2-oxy>-trans-2-butenylamine In accordance with the procedure of example 1-(A) but using 24 grams (0.276 mol) of 4-amino-trans-2-buten-1-ol (bp₁₆: 115° to 116° C.) in place of 24 g (0.276 mol) of 4-amino-cis-2-buten-1-ol and starting with 44 g (0.173 mol) of 2-bromo-4-(1-piperidinomethyl)pyridine, there was obtained 32.5 g (Yield 72%) of the captioned compound as a light brown oily product.

IR(neat, cm⁻¹): 3400, 2950, 1610, 1560, 1420, 1020.

NMR(CDCl₃, ppm): 1.1–1.9 (6H, m), 2.1–2.7 (4H, m), 3.1–3.7 (2H, m), 3.37 (2H, s), 4.1–5.0 (2H, m), 5.7–6.1 (2H, m), 6.65 (1H, s), 6.77 (1H, d), 7.95 (1H, d).

(B)
3-ethoxy-4-[4-<4-(1-piperidinomethyl)pyridyl-2-oxy>-trans-2-butenylamino]-1,2,5-thiadiazole-1-oxide In accordance with the procedure of example 7-(A) but using 4-<4-(1-piperidinomethyl)pyridyl-2-oxy>-trans-2-butenylamine in place of 4-<4-(1-piperidinomethyl)pyridyl-2-oxy->-cis-2-butenylamine, there was obtained 1.50 g (Yield: 80.0%) of the captioned compound in a colorless crystal form.

IR(KBr, cm⁻¹): 3200, 2950, 1600, 1420, 1320, 1100, 855, 720, 580, 530.

NMR(CDCl₃, ppm): 1.2–1.6 (3H, t), 1.2–1.8 (6H, m), 2.1–2.7 (4H, m), 3.37 (2H, s), 3.9–4.3 (2H, m), 4.2–4.7 (2H, q), 4.6–4.9 (2H, m), 5.7–6.1 (2H, m), 6.2–6.7 (1H, b, Eliminated by the D₂O treatment), 6.6–6.9 (2H, m), 7.8–8.1 (1H, d).

(C)
3-amino-4-[4-<4-(1-piperidinomethyl)pyridyl-2-oxy>-trans-2-butenylamino]-1,2,5-thiadiazole-1-oxide In accordance with the procedure of example 7-(B) but using 0.81 g (2 m mol) of the compound obtained in example 9-(B), there was obtained 0.46 g (Yield: 61.2%) of the captioned compound in a colorless crystal form. The melting point of the crystal obtained by recrystallization from methanol was 204° to 205° C., at which temperature it decomposed.

IR(KBr, cm⁻¹): 3300, 2950, 1680, 1620, 1420, 1050

NMR(DMSO-d₆, ppm): 1.1–1.7 (6H, m), 2.0–2.6 (4H, m), 3.34 (2H, s), 3.8–4.2 (2H, m), 4.6–4.9 (2H, m), 5.7–6.0 (2H, m), 6.6 (1H, s), 6.7–6.9 (1H, d), 7.91 (1H, d), 7.5–8.3 (3H, m, Eliminated by the D₂O treatment)

Example 10

Preparation of 3-methylamino-4-[4-<4-(1-piperidinomethyl)pyridyl-2-oxy>-trans-2-butenylamino]-1,2,5-thiadiazole-1-oxide

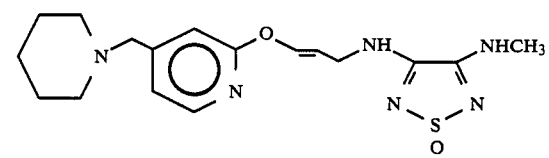

Yield: 67.5%
Melting Point: 100° to 101° C. (Recrystallized from methanol)

IR(KBr, cm⁻¹): 3320, 2950, 1615, 1580, 1415, 1030.

NMR(CDCl₃, ppm): 1.2–1.9 (6H, m), 2.2–2.6 (4H, m), 2.95 (3H, m), 3.7–4.2 (2H, m), 3.86 (2H, s), 4.6–4.9 (2H, m), 5.7–6.0 (2H, m), 6.6 (1H, s), 6.7–6.9 (1H, d), 7.88 (1H, d), 7.7–8.3 (2H, m, Eliminated by the treatment with D₂O)

Example 11

Preparation of
3-amino-4-<4-(4-dimethylaminomethylpyridyl-2-oxy)-cis-2-butenylamino>-1,2,5-thiadiazole-1-oxide

(A)

3-ethoxy-4-<4-(4-dimethylaminomethylpyridyl-2-oxy)-cis-2-butenylamino>-1,2,5-thiadiazole-1-oxide In accordance with the procedure of example 7-(A) but using 2.21 g (0.01 mol) of 4-(4-dimethylaminomethylpyridyl-2-oxy)-cis-2-butenylamine (obtained in Example 3-(A)), there was obtained 2.76 g (Yield: 78.6%) of the captioned compound as a light yellow oily product.

IR(neat, cm$^{-1}$): 3300, 2950, 1620, 1560, 1400, 1380, 1320, 1250, 1120, 1030, 850, 720, 620, 560.

NMR(CDCl$_3$, ppm): 1.3–1.55 (3H, t), 2.25 (6H, s), 3.4 (2H, s), 4.3–4.65 (2H, q), 4.8–5.0 (2H, d), 5.6–5.9 (2H, m), 6.63 (1H, s), 6.7–6.9 (1H, d), 7.2–7.7 (1H, b, Eliminated by the D$_2$O treatment), 7.85–8.0 (1H, d).

(B)

3-amino-4-<4-(4-dimethylaminomethylpyridyl-2-oxy)-cis-2-butenylamino>-1,2,5-thiadiazole-1-oxide In accordance with the procedure of example 7-(B) but using 0.70 g (2 m mol) of the compound obtained in example 11-(A), there was obtained 0.47 g (Yield: 70.0%) of the captioned compound in a colorless crystal form. The melting point of the crystal obtained by recrystallization from methanol was 55° to 60° C.

IR(KBr, cm$^{-1}$): 3250, 3070, 1610, 1580, 1405, 1290, 1150, 1040, 870, 810, 630.

NMR(DMSO-d$_6$/CDCl$_3$, ppm): 2.3 (6H, s), 3.45 (2H, s), 4.0–4,3 (2H, d), 4.7–5.1 (2H, d), 5.55–6.1 (2H, m), 6.67 (1H, s), 6.7–7.0 (1H, d), 7.9–8.1 (1H, m).

Example 12

Preparation of
3-methylamino-4-<4-(4-dimethylaminomethylpyridyl-2-oxy)-cis-2-butenylamino>-1,2,5-thiadiazole-1-oxide

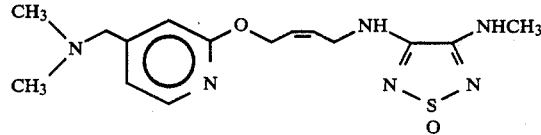

Light Yellow Crystal
Yield: 67.1%

IR(KBr, cm$^{-1}$): 3330, 3150, 3050, 1620, 1415, 1315, 1295, 1160, 1050, 850, 630, 580, 520.

NMR(CDCl$_3$, ppm): 2.3 (6H, s), 3.0 (3H, s), 3.45 (2H, s), 4.1–4.4 (2H, m), 4.8–5.05 (2H, d), 5.7–6.0 (2H, m), 6.7 (1H, s), 6.8–6.95 (1H, d), 7.95–8.15 (1H, d), 8.1–8.6 (1H, b, Eliminated by the treatment with D$_2$O).

Example 13

Preparation of
3-amino-4-[4-<4-(1-piperidinomethyl)pyridyl-2-oxy>-cis-2-butenylamino]-1,2,5-thiadiazole-1,1-dioxide

(A)

3-ethoxy-4-[4-<4-(1-piperidinomethyl)pyridyl-2-oxy>-cis-2-butenylamino]-1,2,5-thiadiazole-1,1-dioxide 2.0 grams (7.65 m mol) of 4-<4-(1-piperidinomethyl)pyridyl-2-oxy>-cis-2-butenylamine (obtained in example 1-(A)) was dissolved in 50 ml of absolute ethanol, added with 1.6 g (7.76 m mol) of 3,4-diethoxy-1,2,5-thiadiazole-1,1-dioxide (prepared by applying the method disclosed in Japanese Patent Laid-Open Publication No. 56-40675), and agitated at room temperature for 24 hours. The solvent was distilled off under reduced pressure, and the residue was passed through a silica gel chromatograph column to purify the same, followed by elution with a mixed solution of ethyl acetate:methanol=4:1. As a result, 1.2 g (Yield: 37%) was obtained as an oily product.

IR(neat, cm$^{-1}$): 3370, 2960, 1630, 1420, 1290, 1150

NMR(CDCl$_3$, ppm): 1.0–1.4 (3H, t), 1.3–1.8 (6H, m), 2.2–2.7 (4H, m), 3.6 (2H, s), 3.4–3.9 (2H, q), 4.0–4.3 (2H, d), 4.7–5.0 (2H, d), 5.7–5.9 (2H, m), 6.6–7.0 (2H, m), 7.85–8.1 (1H, d)

(B)

3-amino-4-[4-<4-(1-piperidinomethyl)pyridyl-2-oxy>-cis-2-butenylamino]-1,2,5-thiadiazole-1,1-dioxide 0.42 g (1 m mol) of a 3-ethoxy product prepared in example 13-(A) was dissolved in 25 ml of ethanol to obtain solution through which dry ammonia gas was passed at 5° C. of solution temperature for 20 minutes, followed by agitation at room temperature for an additional 2 hours. The solvent was distilled off under reduced pressure after the completion of the reaction, and the residue was passed through a silica gel chromatograph column to purify the same, followed by elution with a mixed solution of ethyl acetate:methanol=4:1. As a result, 0.22 g (Yield: 56.3%) was obtained in a light yellow crystal form. The melting point of the crystal was 218° to 225° C., at which the crystal decomposed.

IR(KBr, cm$^{-1}$): 3600, 3370, 1640, 1260, 1150

NMR(CMSO-d$_6$, ppm): 1.3–1.7 (6H, m), 2.3–2.6 (4H, m), 3.5 (2H, s), 3.5–3.9 (2H, b, Eliminated by the D$_2$O treatment), 3.9–4.1 (2H, d), 4.7–4.9 (2H, d), 5.5–5.8 (2H, m), 6.6 (1H, s), 6.7–6.9 (1H, d), 7.9–8.05 (1H, d).

Example 14

Preparation of
3-methylamino-4-[4-<4-(1-piperidinomethyl)pyridyl-2-oxy>-cis-2-butenylamino]-1,2,5-thiadiazole-1,1-dioxide

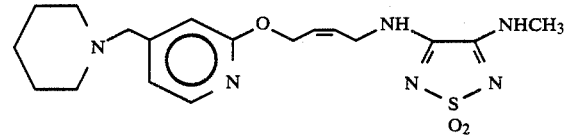

Light Yellow Crystal
Yield: 49.3%.

IR(KBr, cm$^{-1}$): 3350, 2960, 1640, 1420, 1310, 1165, 1030.

NMR(CDCl$_3$, ppm): 1.3–1.8 (6H, m), 2.2–2.55 (4H, m), 3.05 (3H, s), 3.35 (2H, s), 4.05–4.3 (2H, d), 4.7–4.95 (2H, d), 5.65–5.85 (2H, m), 6.6 (1H, s), 6.7–6.9 (1H, d), 7.4–7.65 (2H, b, Eliminated by the treatment with D$_2$O), 7.8–8.0 (1H, d).

Example 15

Preparation of 3-amino-4-[4-<4-(1-piperidinomethyl)pyridyl-2-oxy>-cis-2-butenylamino]-1,2,5-thiadiazole (A)

N-[4-<4-(1-piperidinomethyl)pyridyl-2-oxy>-cis-2-butenyl]ethanediimidamide.tetrahydrochloride 3.76 g (0.01 mol) of 3-amino-4-[4-<4-(1-piperidinomethyl)pyridyl-2-oxy>-cis-2-butenylamino]-1,2,5-thiadiazole-1-oxide obtained in example 7-(B) was dissolved in 89 ml of methanol, added with 7.13 ml of conc. hydrochloric acid while cooling at 5° C., and agitated at room temperature for 4 hours. The reaction mixture obtained was concentrated under reduced pressure after the completion of the reaction, and 8.9 ml of 2-propanol was added to the mixture followed by concentration under reduced pressure. This procedure was repeated three times, and water was removed by azetotropic distillation. The residue was added with 2.7 ml of absolute ethanol, ground thoroughly and cooled. Then the deposited crystal was quickly collected by filtration. The crystal obtained was used in the next reaction after drying without purification because of its high hygroscopicity.

(B)

3-amino-4-[4-<4-(1-piperidinomethyl)pyridyl-2-oxy>-cis-2-butenylamino]-1,2,5-thiadiazole 2.22 grams of N,N'-thiobisphthalimide (prepared by the method described in M. V. Kalnins, Canadian Journal of Chem., 44, 2111 (1966)) was added slowly to a mixture of 1.08 g of the crude crystal obtained in example 15-(A), 10 ml of $CH_2Cl_2$ and 0.69 g of triethylamine at room temperature under agitation, followed by agitation at room temperature for an additional 2 hours. The reaction mixture was added with 10 ml of 20% KOH aqueous solution and shaken thoroughly after the completion of the reaction; then the organic solvent layer was separated and dried with $MgSO_4$. The solvent was distilled off under reduced pressure, and the residue was passed through a silica gel chromatograph column to purify the same, followed by elution with a mixed solution of ethyl acetate:methanol:aqueous ammonia=6:1:1. As a result, 0.29 g (Yield: 35.3%) was obtained as a light yellow oily product.

IR(neat, $cm^{-1}$): 3390, 3250, 2950, 1620, 1565, 1420, 1300, 1170, 1040, 990, 830, 770.

NMR($CDCl_3$, ppm): 1.1–1.9 (6H, m), 2.1–2.7 (4H, m), 3.35 (2H, s), 3.8–4.3 (2H, m), 4.7–5.0 (2H, d), 5.3–5.6 (2H, b, Eliminated by the $D_2O$ treatment), 5.4–5.9 (2H, m), 6.55 (1H, s), 6.6–6.8 (1H, d), 7.75–8.0 (1H, d).

Example 16

Preparation of 3-amino-4-<4-(4-dimethylaminomethylpyridyl-2-oxy)-cis-2-butenylamino>-1,2,5-thiadiazole In accordance with the procedure of example 15-(A) and 15-(B) but using 3.36 grams (0.01 mol) of 3-amino-4-<4-(4-dimethylaminomethylpyridyl-2-oxy)-cis-2-butenylamino>-1,2,5-thiadiazole-1-oxide obtained in example 11-(B), there was obtained 0.28 g (Yield: 8.8%) of the captioned compound as a light yellow oily product.

IR(neat, $cm^{-1}$): 3400, 3300, 1620, 1570, 1300, 1250, 1025, 825, 770, 620.

NMR($CDCl_3$, ppm): 2.25 (6H, s), 3.37 (2H, s), 3.75–4.2 (2H, d), 4.65–4.95 (2H, d), 5.15–5.6 (3H, b, Eliminated by the $D_2O$ treatment), 5.5–5.85 (2H, m), 6.65 (1H, s), 6.6–6.8 (1H, d), 7.8–8.0 (1H, d).

Example 17

Preparation of 2-amino-5-[4-<4-(1-piperidinomethyl)pyridyl-2-oxy>-cis-2-butenylamino]-1,3,4-thiadiazole (A)

2-bromo-5-[4-<4-(1-piperidinomethyl)pyridyl-2-oxy>-cis-2-butenylamino]-1,3,4-thiadiazole 1.5 grams (5.7 m mol) of 4-<4-(1-piperidinomethyl)pyridyl-2-oxy>-cis-2-butenylamine (obtained in example 1-(A)) was dissolved in 20 ml of ethanol, added with 1.4 g (5.7 m mol) of 2,5-dibromo-1,3,4-thiadiazole (prepared by the method described in R. Stolle and K. Fehrenbach, J. Prakt. Chem., 122, 289 (1929)) and 1 ml of triethylamine, and then refluxed for 10 hours. The solvent was distilled off under reduced pressure after the completion of the reaction, and the residue was passed through a silica gel chromatograph column for purification, followed by elution with ethyl acetate. As a result, 0.82 g (Yield: 36%) of the captioned compound was obtained in a colorless crystal form. The melting point of the crystal obtained by recrystallization from methanol was 121.5° to 123° C.

IR(KBr, $cm^{-1}$): 3360, 2930, 1610, 1530, 1410, 1290, 1040.

MMR($CDCl_3$, ppm): 1.4–1.8 (6H, m), 2.2–2.6 (4H, m), 3.35 (2H, s), 4.0–4.2 (2H, d), 4.8–5.0 (2H, d), 5.6–5.9 (2H, m), 6.6 (1H, s), 6.7–7.0 (1H, d), 7.2–7.4 (1H, b, Eliminated by the $D_2O$ treatment), 7.85–8.05 (1H, d).

(B)

2-amino-5-[4-<4-(1-piperidinomethyl)pyridyl-2-oxy>-cis-2-butenylamino]-1,3,4-thiadiazole 0.7 grams (1.78 m mol) of the bromo product obtained in example 17-(A) was dissolved in 15 ml of 10% ammoniamethanol solution, and reacted in a sealed tube at 100° C. for 2 hours. The solvent was distilled off under reduced pressure after the completion of the reaction, and the residue was passed through a silica gel chromatograph column for purification, followed by elution with a mixed solution of ethyl acetate:methanol=9:1. Whereupon, 0.22 g (Yield: 34%) of the captioned compound was obtained as a colorless crystal having a melting point of 85° to 90° C.

IR(KBr, $cm^{-1}$): 3200, 2940, 1610, 1560, 1420, 1285

NMR($CDCl_3$): 1.3–1.6 (6H, m), 2.0–2.25 (4H, m), 3.2 (2H, s), 3.6–3.8 (2H, d), 4.5–4.7 (2H, d), 5.4–5.7 (2H, m), 6.5 (1H, s), 6.6–6.8 (1H, d), 7.0–7.7 (3H, b, Eliminated by the $D_2O$ treatment), 7.75–8.0 (1H, d).

Example 18

Preparation of 2-methylamino-5-[4-<4-(1-piperidinomethyl)pyridyl-2-oxy>-cis-2-butenylamino]-1,3,4-thiadiazole

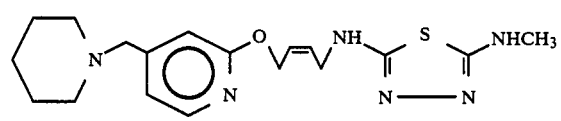

Yield: b 21%
Melting Point: 53° to 55° C.

IR(KBr, cm⁻¹): 3280, 2950, 1620, 1510, 1410, 1040

NMR(CDCl₃, ppm): 1.3–1.7 (6H, m), 2.2–2.5 (4H, m), 3.35 (3H, s), 3.4 (2H, s), 3.75–4.05 (2H, m), 3.55–3.7 (1H, m, Eliminated by the treatment with D₂O), 5.5–5.8 (2H, m), 6.6 (1H, s), 6.7–6.9 (1H, d), 7.8–8.0 (1H, d)

Example 19

Preparation of
3-amino-1-methyl-5-[4-<4-(1-piperidinomethyl)pyridyl-2-oxy>-cis-2-butenylamino]-1H-1,2,4-triazole (A)

N-cyano-S-methyl-N'-[4-<4-(1-piperidinomethyl)pyridyl-2-oxy>-cis-2-butenyl]-isothiourea 2.0 grams (7.7 m mol) of 4-<4-(1-piperidinomethyl)pyridyl-2-oxy>-cis-2-butenyamine (obtained in example 1-(A)) and 1.22 g (8.36 m mol) of dimethylcyanodithioimidecarbonate (prepared by the method described in Japanese Patent Publication No. 46-26482) were dissolved in 20 ml of methanol and agitated at room temperature for 16 hours. The solvent was distilled off under reduced pressure after completion of the reaction, and the residue was passed through a silica gel chromatograph column for purification, followed by elution with ethyl acetate. As a result, 0.95 g (Yield: 34.5%) of the captioned compound having a melting point of 107° C. was obtained.

IR(KBr, cm⁻¹): 3250, 2940, 2170, 1610, 1550, 1520.

NMR(CDCl₃, ppm): 1.4–1.7 (6H, m), 2.2–2.5 (4H, m), 3.32 (3H, s), 3.95–4.23 (2H, m), 4.75–4.9 (2H, m), 5.6–5.8 (2H, m), 6.6–7.0 (3H, m, 1H was eliminated by the D₂O treatment), 7.9 (1H, d).

MS: M⁺=359.

(B)

3-amino-1-methyl-5-[4-<4-(1-piperidinomethyl)pyridyl-2-oxy>-cis-2-butenylamino]-1H-1,2,4-triazole 0.85 g (2.37 m mol) of the compound obtained in (A) above was dissolved in 30 ml of ethanol, and added with 0.9 ml of methylhydrazine followed by reflux for 16 hours. The solvent was distilled off under reduced pressure after the completion of the reaction, and the residue was passed through a silica gel chromatograph column for purification. As a result, 0.6 g (Yield: 71%) of the captioned compound was obtained as a colorless yellow oily product.

IR(neat, cm⁻¹): 3350, 3200, 2950, 2870, 2800, 1610, 1550, 1480, 1420.

NMR(CDCl₃, ppm): 1.4–1.8 (6H, m), 2.25–2.5 (4H, m), 3.32 (3H, s), 3.38 (2H, s), 3.6–4.2 (2H, m) 4.75–5.0 (2H, m), 5.3–6.2 (4H, m, 2H were eliminated by the D₂O treatment), 6.6 (1H, s), 6.7–6.9 (1H, d), 7.9 (1H, d).

MS: M⁺=357.

Example 20

Preparation of
2-[4-<4-(1-piperidinomethyl)pyridyl-2-oxy>-cis-2-butenylamino]-1H-pyrimidin-4-one 1.55 g (5.93 m mol) of 4-<4-(1-piperidinomethyl)pyridyl-2-oxy>-cis-2-butenylamine (obtained in example 1-(A)) and 0.85 g (5.98 m mol) of 2-methylthio-1H-pyrimidin-4-one were melted at 150° C. for 1.5 hours. The mixture obtained was dissolved in a small amount of methanol after the completion of the reaction and passed through a silica gel chromatograph column for purification, followed by elution with an ethyl acetate:methanol=4:1. As a result, 1.1 g (Yield: 52%) of the captioned compound was obtained as a colorless oily product.

IR(neat, cm⁻¹): 3250, 2940, 1670, 1610, 1310, 1040

NMR(CDCl₃, ppm): 1.35–1.8 (6H, m), 2.2–2.5 (4H, m), 3.35 (2H, s), 4.0–4.2 (2H, d), 4.7–4.9 (2H, d), 5.5–5.75 (1H, d), 5.6–5.9 (2H, m), 6.6 (1H, s), 6.7–6.9 (1H, d), 7.4–7.6 (1H, d), 7.8–8.0 (1H, d).

Example 21

Preparation of
5-dimethylaminomethyl-2-[4-<4-(1-piperidinomethyl)pyridyl-2-oxy>-cis-2-butenylamino]-1H-pyrimidin-4-one

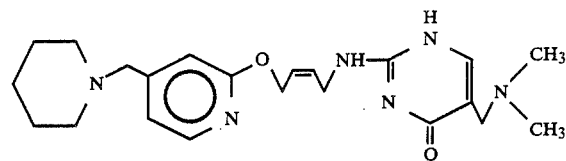

Colorless Oily Product.

Yield: 17%.

IR(neat, cm⁻¹): 3290, 2950, 1660, 1300, 1035.

NMR(CDCl₃, ppm): 1.4–1.7 (6H, m), 2.2–2.5 (4H, m), 2.3 (6H, s), 3.35 (2H+2H, s), 3.9–4.1 (2H, d), 4.8–5.0 (2H, d), 5.6–5.85 (2H, m), 5.9–6.3 (2H, b, Eliminated by the treatment with D₂O), 6.5–6.9 (2H, m), 7.55 (1H, s), 7.85–8.0 (1H, d).

Example 22

Preparation of
2-[4-<4-(1-piperidinomethyl)pyridyl-2-oxy>-cis-2-butenylamino]-5-(3-pyridylmethyl)-1H-pyrimidin-4-one 1.24 grams (4.75 m mol) of 4-<4-(1-piperidinomethyl)pyridyl-2-oxy>-cis-2-butenylamine and 1.5 g (6.07 m mol) of 2-nitroamino-5-(3-pyridylmethyl)-1H-pyrimidin-4-one were refluxed in 30 ml of pyridine under agitation for 20 hours. The solvent was distilled off under reduced pressure after the completion of the reaction, and the residue was passed through a silica gel chromatograph column for purification, followed by elution with a mixed solution of ethyl acetate:methanol=4:1. Whereupon, 1.0 g (Yield: 47%) of the captioned compound was obtained as a colorless oily product.

IR(neat, cm⁻¹): 3250, 3050, 2950, 2860, 1660, 1610, 1560, 1480.

NMR(DMSO-d₆, ppm): 1.4–1.7 (6H, m), 2.15–2.40 (4H, m), 3.35 (2H, s), 3.52 (2H, s), 3.8–4.1 (2H, m), 4.7–4.95 (2H, m), 5.5–5.7 (2H, m), 6.0–8.4 (10H, m, 2H were eliminated by the D₂O treatment).

MS: M⁺=446.

Example 23

Preparation of
5-(3-dimethylaminomethylbenzyl)-2-[4-<4-(1-piperidinomethyl)pyridyl-2-oxy>-cis-2-butenylamino]-1H-pyrimidin-4-one 3.3 grams (12.6 m mol) of 4-<4-(1-piperidinomethyl)pyridyl-2-oxy>-cis-2-butenylamine and 4.8 g (14.8 m mol) of 2-nitroamino-5-(3-dimethylaminomethylbenzyl)-1H-pyrimidin-4-one were refluxed in 90 ml of pyridine under agitation for 20 hours. The solvent was distilled off under reduced pressure after the completion of the reaction, and the residue was passed through a silica gel chromatograph column for purification, followed by elution with a mixed solution of ethyl acetate:methanol:ammonia=6:1:1. As a result, 1.1 g (Yield: 17.4%) of the captioned compound was obtained as a light brown oily product.

IR(neat, cm$^{-1}$): 3300, 2970, 2900, 2850, 1660, 1615, 1565.

NMR(CDCl$_3$, ppm): 1.35-1.75 (6H, m), 2.15 (6H, s), 2.15-2.5 (4H, m), 3.28 (4H, s), 3.55 (2H, s), 3.85-4.1 (2H, m), 4.7-4.9 (2H, m), 5.5-5.7 (2H, m), 6.5-8.5 (10H, m, 2H were eliminated by the D$_2$O treatment).

Example 24

Preparation of
5-(3-dimethylaminomethylbenzyl)-2-<4-(4-dimethylaminomethylpyridyl-2-oxy)-cis-2-butenylamino>-1H-pyrimidin-4-one

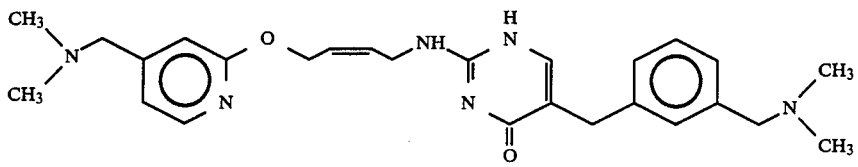

Yield: 43%.

IR(neat, cm$^{-1}$): 3275, 2960, 2850, 2800, 1660, 1610, 1565.

NMR(CDCl$_3$, ppm): 2.15 (6H, s), 2.18 (6H, s), 3.29 (4H, s), 3.55 (2H, s), 3.9-4.1 (2H, m), 4.1-4.7 (2H, b, Eliminated by the treatment with D$_2$O), 4.7-4.9 (2H, m), 5.6-5.8 (2H, m), 6.5-8.0 (8H, m).

MS: M$^+$=462.

Example 25

Preparation of
3-[4-<4-(1-piperidinomethyl)pyridyl-2-oxy>-cis-2-butenylamino]-6-(3-pyridylmethyl)-1,2,4-triazin-5-one

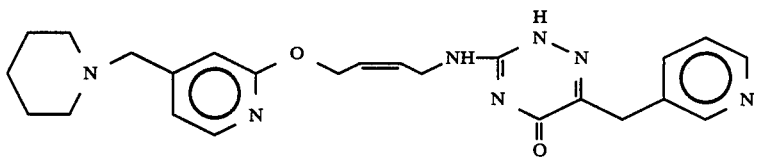

Colorless Crystal.
Yield: 20%.
Melting Point: 134° to 135° C.
IR(KBr, cm$^{-1}$): 3250, 2950, 1660, 1420, 1020.
NMR(DMSO-d$_6$, ppm): 1.1-1.8 (6H, m), 2.0-2.6 (4H, m), 3.34 (2H, s), 3.79 (2H, s), 3.7-4.2 (2H, m), 4.6-5.0 (2H, m), 5.4-5.7 (2H, m), 6.61 (1H, s), 6.79 (1H, d), 7.4-7.7 (1H, m), 8.2-8.5 (2H, m)

Example 26

Preparation of
4-amino-6-[4-<4-(1-piperidinomethyl)pyridyl-2-oxy>-cis-2-butenylamino]-1H-pyrimidin-2-one 2.0 grams (7.66 m mol) of 4-<4-(1-piperidinomethyl)pyridyl-2-oxy>-cis-2-butenylamine and 0.23 g (1.26 m mol) of 4-amino-6-chloro-1H-pyrimidin-2-one hydrochloride were refluxed in 3 ml of water under agitation for 30 minutes. The deposited crystal was filtered after the completion of the reaction and recrystallized from a mixed solvent of methanol and dimethylsulfoxide. As a result, 0.32 g (Yield: 68.0%) of the captioned compound was obtained in a colorless crystal form. The melting point of the crystal obtained was 224.7° C., at which temperature it decomposed.

IR(KBr, cm$^{-1}$): 3350, 3150, 3050, 2950, 1650, 1610, 1520, 1420.

NMR(DMSO-d$_6$, ppm): 1.3-1.6 (6H, m), 2.2-2.5 (4H, m), 3.6 (2H, s), 3.8-4.0 (2H, m), 4.7 (1H, s), 4.75-4.9 (2H, m), 5.45-5.7 (2H, m), 6.2-6.4 (3H, b, Eliminated by the D$_2$O treatment), 6.6-8.0 (3H, m).

Example 27

Preparation of
6-amino-5-[4-<4-(1-piperidinomethyl)pyridyl-2-oxy>-cis-2-butenylamino]-1,2,4-triazin-3-one 1.0 grams (3.83 m mol) of 4-4-(1-piperidinomethyl)-pyridyl-2-oxy-cis-2-butenylamine and 0.6 g (3.8 m mol) of 6-amino-5-methylmercapto-1,2,4-triazin-3-one were

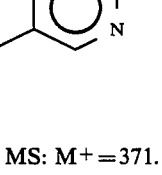

stirred in 40 ml of ethanol at room temperature for 24 hours. The deposited crystal was filtrated after the completion of the reaction and recrystallized from ethanol. As a result, 0.73 g (Yield: 51%) of the captioned compound was obtained as a colorless crystal having a melting point of 170° to 180° C.

IR(KBr, cm$^{-1}$): 3250, 2950, 1640, 1560, 1460, 1030

NMR(DMSO-d$_6$, ppm): 1.3-1.8 (6H, m), 2.1-2.5 (4H, m), 3.35 (2H, s), 4.0-4.3 (2H, m), 4.7-5.0 (2H, m), 5.37 (2H, b, Eliminated by the D$_2$O treatment), 6.61 (1H, s), 6.78 (1H, d), 7.5-8.0 (1H, b, Eliminated by the D$_2$O treatment), 7.92 (1H, d), 11.42 (1H, b, Eliminated by the D$_2$O treatment)

MS: M$^+$=371.

Example 28

Preparation of
6-methylamino-5-[4-<4-(1-piperidinomethyl)pyridyl-2-oxy>-cis-2-butenylamino]-1,2,4-triazin-3-one In accordance with the procedure of example 27 but using 1.2 grams (4.59 m mol) of 4-<4-(1-piperidinomethyl)pyridyl-2-oxy>-cis-2-butenylamine and 0.726 g (4.59 m mol) of 6-methylamino-5-mercapto-1,2,4-triazin-3-one, there was obtained 0.75 g (Yield: 42%) of the captioned compound in a colorless crystal form. The melting point of the crystal was 150° to 160° C., at which temperature it decomposed.

IR(KBr, cm$^{-1}$): 3350, 2950, 1640, 1600, 1400, 1040

NMR(DMSO-d$_6$, ppm): 1.2-1.8 (6H, m), 2.2-2.5 (4H, m), 3.69 (3H, d), 3.8-4.3 (2H, m), 4.7-5.0 (2H, m), 5.4-6.6 (2H, m), 6.54 (1H, s), 6.71 (1H, d), 7.29 (1H, d) wherein 5.4-6.6 (1H, b), 7.2-7.6 (1H, b) and 11.43 (1H, b) were eliminated by the D$_2$O treatment.

MS: M+=385.

Example 29

Preparation of
6-amino-2-methyl-5-[4-<4-(1-piperidinomethyl)pyridyl-2-oxy>-cis-2-butenylamino]-1,2,4-triazin-3-one Colorless Oily Product.
Yield: 43%.
IR(neat, cm$^{-1}$): 3350, 2950, 1650, 1350, 1030
NMR(CDCl$_3$, ppm): 1.2-1.8 (6H, m), 2.2-2.6 (4H, m), 3.38 (3H, s), 3.36 (2H, s), 4.0-4.3 (2H, m), 4.7-5.0 (2H, m), 5.3-5.5 (2H, m), 5.2-6.1 (2H, b, Eliminated by the treatment with D$_2$O), 6.56 (1H, s), 6.69 (1H, d), 7.93 (1H, d), 8.46 (1H, b, Eliminated by the treatment with D$_2$O).
MS: M+=385.

Example 30

Preparation of
6-amino-5-[4-<4-(1-piperidinomethyl)pyridyl-2-oxy>-trans-2-butenylamino]-1,2,4-triazin-3-one Colorless Crystal.
Yield: 46.8%.
Melting Point: 200° to 205° C. (d).
IR(KBr, cm$^{-1}$) 3250, 2950, 1640, 1460, 1300, 1020.
NMR(DMSO-d$_6$, ppm): 1.2-1.8 (6H, m), 2.1-2.4 (4H, m), 3.32 (2H, s), 3.8-4.2 (2H, m), 4.6-4.9 (2H, m), 5.7-6.0 (2H, m), 6.59 (1H, s), 6.79 (1H, d), 7.87 (1H, d); 5.48 (1H, b), 7.5-7.9 (1H, b) and 11.48 (1H, b) were eliminated by the D$_2$O treatment.
MS: M+=371.

Example 31

Preparation of
6-amino-5-<4-(4-dimethylaminomethylpyridyl-2-oxy)-cis-2-butenylamino>-1,2,4-triazin-3-one In accordance with the procedure of example 25 but using 0.7 grams (3.16 m mol) of 4-(4-dimethylaminomethylpyridyl-2-oxy)-cis-2-butenylamine (example 3-(A)) and 0.45 g (3.16 m.mol) of 6-amino-5-mercapto-1,2,4-triazin-3-one, there was obtained 0.65 g (Yield: 62%) of the captioned compound as a colorless crystal having a melting point of 180° to 190° C. (d).
IR(KBr, cm$^{-1}$): 3200, 2800, 1650, 1470, 1295, 1025.
NMR(DMSO-d$_6$, ppm): 2.15 (6H, s), 2.28 (2H, s), 3.9-4.4 (2H, m), 4.6-5.0 (2H, m), 5.5-5.9 (2H, m), 6.54 (1H, s), 7.71 (1H, d), 7.88 (1H, d); 5.27 (2H, b), 7.5-7.9 (1H, b) and 11.42 (1H, b) were eliminated by the D$_2$O treatment.

MS: M+=331.

Example 32

Preparation of
1-amino-2-[4-<6-(1-piperidinomethyl)pyridyl-2-oxy>-cis-2-butenylamino]-1-cyclobuten-3,4-dione (A)
4-<6-(1-piperidinomethyl)pyridyl-2-oxy>-cis-2-butenylamine 2.34 grams of 60% sodium hydride was dispersed in 50 ml of absolute tetrahydrafuran and slowly added with 5.1 g (0.0586 mol) of 4-amino-cis-2-buten-1-ol. The reaction solution was cooled after agitation at 50° C. for 30 minutes, and then slowly added with 12.5 g (0.049 mol) of 2-bromo-6-(1-piperidinomethyl)pyridine (prepared by applying the method described in Japanese Patent Laid-Open Publication No. 58-170779) in 13 ml of tetrahydrofuran and refluxed for 72 hours under agitation. The solvent was distilled off under reduced pressure after the completion of the reaction, and the residue was added with 200 ml of water and extracted with 200 ml of dichloromethane four times. The solvent was distilled off after drying an organic layer with magnesium sulfate anhydrous, and the residue was passed through a silica gel chromatograph column for purification, followed by elution with a mixed solution of ethyl acetate:methanol=4:1. As a result, 7.05 g (Yield: 55.1%) of the captioned compound was obtained as a light brown oily product.
NMR(CDCl$_3$, ppm): 1.3-1.8 (6H, m), 2.2-2.65 (4H, m), 2.75 (2H, s), 3.2-3.5 (2H, m), 4.7-5.0 (2H, d), 5.5-5.8 (2H, t), 6.25-7.6 (3H, m)

(B)
1-methoxy-2-[4-<6-(1-piperidinomethyl)pyridyl-2-oxy>-cis-2-butenylamino]-1-cyclobuten-3,4-dione 1.704 grams (0.012 mol) of dimethyl squalate (prepared by the process reported by Sideny Cohen et al, in J. Amer. chem. Soc., Vol. 88, 1533 (1966)) was dissolved in 50 ml of absolute methanol and cooled at 5° C. Then a solution of 3.132 grams (0.012 mol) of 4-6-(1-piperidinomethyl)pyridyl-2-oxy-cis-2-butenylamine which was prepared by the method described in example 32-(A) in 20 ml of absolute methanol was dropped into the dimethyl squalate solution obtained above at 5° C. of solution temperature, with stirring, and was stirred at room temperature for an additional 6 hours. The solvent was distilled off under reduced pressure after the completion of the reaction, and the residue was passed through a silica gel chromatograph column to purify the same, followed by elution with a mixed solution of ethyl acetate:methanol=4:1. As a result, 4.24 g (Yield: 95.3%) of the captioned compound was obtained as a light yellow oily product.

IR(neat, cm$^{-1}$): 3350, 2970, 2850, 1810, 1718, 1615, 1460, 1385, 1035, 930, 810.

NMR(CDCl$_3$, ppm): 1.2–1.9 (6H, m), 2.15–2.8 (4H, m), 3.5 (2H, s), 4.0–4.4 (2H, m), 4.7–5.1 (2H, m), 4.3 (3H, s), 5.5–5.9 (2H, m), 6.4–7.6 (3H, m).

(C)

1-amino-2-[4-<6-(1-piperidinomethyl)pyridyl-2-oxy>-cis-2-butenylamino]-1-cyclobuten-3,4-dione 3.71 grams (0.01 mol) of 1-methoxy-2-[4-<6-(1-piperidinomethyl)pyridyl-2-oxy>-cis-2-butenylamino]-1-cyclobuten-3,4-dione obtained in (B) above was dissolved in 50 ml of absolute methanol to obtain a solution through which dry ammonia gas was passed at 50° C. of reaction temperature for 20 minutes, and then the solution was stirred at room temperature for an additional 2 hours. The deposited crystal was suctionally firtlated after the completion of the reaction, and recrystallized from methanol. As a result, 2.4 g (Yield: 67.5%) of the captioned compound having a melting point of 205° to 210° C. (d) was obtained as a colorless crystal.

IR(KBr, cm$^{-1}$): 3330, 3150, 2950, 1810, 1650, 1305, 1260, 1150, 1020, 985, 860, 800, 595.

NMR(DMSO-d$_6$+CDCl$_3$, ppm): 1.1–1.7 (6H, m), 2.05–2.6 (4H, m), 2.8–3.2 (1H, bro, Eliminated by the D$_2$O treatment), 3.4 (2H, s), 3.5–4.0 (2H, bro, Eliminated by the D$_2$O treatment), 4.1–4.4 (2H, m), 4.6–5.0 (2H, m), 5.4–5.9 (2H, m), 6.3–7.6 (3H, m).

Example 33

Preparation of 1-methylamino-2-[4-<6-(1-piperidinomethyl)pyridyl-2-oxy>-cis-2-butenylamino]-1-cyclobuten-3,4-dione

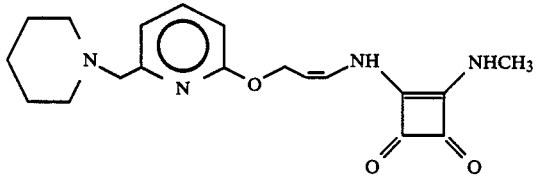

Colorless Crystal.
Yield: 64.9%.
Melting Point: 203° to 206° C. (d).
IR(KBr, cm$^{-1}$): 3330, 3150, 2950, 1810, 1650, 1450, 1305, 1260, 1150, 1022, 990, 860, 800, 730, 600.

NMR(DMSO-d$_6$/CDCl$_3$, ppm): 1.2–1.8 (6H, m), 2.2–2.6 (4H, m), 3.4 (3H, s), 4.0–4.5 (2H, m), 4.6–5.0 (2H, m), 5.4–5.8 (2H, m), 6.3–7.6 (3H, m), 7.1–7.4 (1H, bro, Eliminated by the treatment with D$_2$O).

Example 34

Preparation of 3-amino-4-[4-<6-(1-piperidinomethyl)pyridyl-2-oxy>-cis-2-butenylamino]-1,2,5-thiadiazole-1-oxide (A)
3-ethoxy-4-[4-<6-(1-piperidinomethyl)pyridyl-2-oxy>-cis-2-butenylamino]-1,2,5-thiadiazole-1-oxide 3.0 grams (0.0115 mol) of 4-<6-(1-piperidinomethyl)pyridyl-2-oxy>-cis-2-butenylamine was dissolved in 50 ml of absolute ethanol, added with 2.1 g (0.0119 mol) of 3,4-diethoxy-1,2,5-thiadiazole-1-oxide (prepared by applying the method described in Japanese Patent Laid-Open Publication No. 56-40675) and agitated at room temperature for 2 hours. The solvent was distilled off under reduced pressure after the completion of the reaction, and the residue was passed through a silica gel chromatograph column for purification, followed by elution with a mixed solution of ethyl acetate:methanol=4:1. As a result, 4.5 g (Yield: 96.6%) of the captioned compound was obtained as a colorless oily product.

IR(neat, cm$^{-1}$): 3300, 2950, 1620, 1455, 1380, 1340, 1250, 1120, 1030, 805, 720, 620, 570, 530.

NMR(CDCl$_3$, ppm): 1.2–1.6 (3H, t), 1.3–1.9 (6H, m), 2.2–2.7 (4H, m), 3.5 (2H, s), 4.0–4.5 (2H, m), 4.3–4.7 (2H, q), 4.8–5.2 (2H, m), 5.5–6.0 (2H, m), 6.3–7.7 (3H, m).

(B)

3-amino-4-[4-<6-(1-piperidinomethyl)pyridyl-2-oxy>-cis-2-butenylamino]-1,2,5-thiadiazole-1-oxide 1.0 grams (0.00247 mol) of 3-ethoxy-4-<4-6-(1-piperidinomethyl)pyridyl-2-oxy>-cis-2-butenylamino-1,2,5-thiadiazole-1-oxide obtained in example 34-(A) was dissolved in 40 ml of absolute ethanol, added with 2 ml of ethanol solution saturated with ammonia gas and agitated at room temperature for 30 minutes. The solvent was distilled off under reduced pressure after the completion of the reaction, and the residue was passed through a silica gel chromatograph column for purification, followed by elution with a mixed solution of ethyl acetate:methanol=4:1. As a result, 0.53 g (Yield: 57.1%) of the captioned compound having a melting point of 60° to 63° C. was obtained as a colorless crystal.

IR(KBr, cm$^{-1}$): 3350, 3300, 3200, 2960, 1675, 1580, 1460, 1435, 1315, 1265, 1160, 1040, 1000, 880, 800, 660

NMR(DMSO-d$_6$/CDCl$_3$, ppm): 1.2–1.9 (6H, m), 2.1–2.7 (4H, m), 3.5 (2H, s), 3.9–4.4 (2H, m), 4.6–5.1 (2H, m), 5.4–5.9 (2H, m), 6.3–7.4 (3H, m), 7.1–7.8 (2H, bro, Eliminated by the D$_2$O treatment.).

Example 35

Preparation of 3-methylamino-4-[4-<6-(1-piperidinomethyl)pyridyl-2-oxy>-cis-2-butenylamino]-1,2,5-thiadiazole-1-oxide

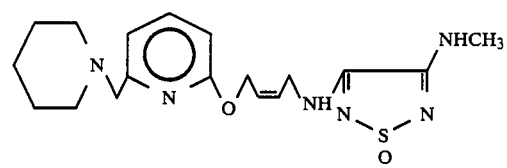

Light Yellow Crystal.
Yield: 42.6%.
IR (KBr, cm$^{-1}$): 3320, 2950, 1610, 1450, 1305, 1260, 1305, 1260, 1160, 1040, 850, 800, 735, 620.

NMR(DMSO-d$_6$, ppm): 1.1–1.9 (6H, m), 2.2–2.7 (4H, m), 2.95 (3H, s), 3.55 (2H, s), 3.9–4.4 (2H, m), 4.6–5.1 (2H, m), 5.4–6.0 (2H, m), 6.3–7.6 (3H, m).

Example 36

Preparation of
3-amino-4-[4-<6-(1-piperidinomethyl)pyridyl-2-oxy>-cis-2-butenylamino]-1,2,5-thiadiazole-1,1-dioxide (A)
3-ethoxy-4-[4-<6-(1-piperidinomethyl)pyridyl-2-oxy>-cis-2-butenylamino]-1,2,5-thiadiazole-1,1-dioxide 1.305 grams (0.005 mol) of the amine obtained in example 32-(A) was dissolved in 50 ml of absolute ethanol, added with 1.03 g (0.05 mol) of 3,4-diethoxy-1,2,5-thiadiazole-1,1-dioxide (generated by applying the method described in Japanese Patent Laid-Open Publication No. 56-40675) and agitated at room temperature for 24 hours. The solvent was distilled off under reduced pressure after the completion of the reaction, and the residue was passed through a silica gel chromatograph column for purification, followed by elution with a mixed solution of ethyl acetate:methanol=4:1. As a result, 1.59 g (Yield: 75.5%) of the captioned compound was obtained as an oily product.

(B)
3-amino-4-[4-<6-(1-piperidinomethyl)pyridyl-2-oxy>-cis-2-butenylamino]-1,2,5-thiadiazole-1,1-dioxide 0.90 grams (0.00214 mol) of the ethoxy compound prepared in example 36-(A) was dissolved in 45 ml of absolute ethanol, added with 2 ml of methanol solution saturated with ammonia at room temperature and agitated at room temperature for 2 hours. The solvent was distilled off under reduced pressure after the completion of the reaction, and the residue was passed through a silica gel chromatograph column for purification, followed by elution with a mixed solution of ethyl acetate:methanol=4:1. As a result, 0.50 g (Yield: 59.6%) of the captioned compound having a melting point of 68° to 72° C. was obtained as a light yellow crystal.

IR(KBr, cm$^{-1}$): 3300, 2900, 1670, 1630, 1595, 1440, 1295, 1140, 1020, 980, 850, 640.

NMR(DMSO-d$_6$—DCCl$_3$, ppm); 1.2–1.8 (6H, m), 2.1–2.6 (4H, m), 3.4 (2H, s), 3.8–4.2 (2H, m), 4.6–4.9 (2H, m), 5.5–5.9 (2H, m), 6.3–7.7 (3H, m).

Example 37

Preparation of
3-methylamino-4-[4-<6-(1-piperidinomethyl)pyridyl-2-oxy>-cis-2-butenylamino]-1,2,5-thiadiazole-1,1-dioxide

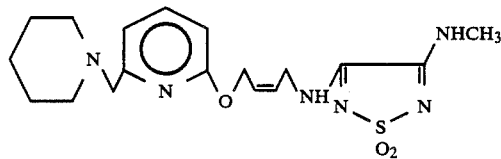

Light Yellow Crystal.
Yield: 51.8%.
Melting Point: 50° to 54° C.
IR(KBr, cm$^{-1}$): 3300, 2900, 1630, 1440, 1400, 1300, 1150, 900, 750, 630, 540.
NMR(CDCl$_3$, ppm): 1.2–1.7 (6H, m), 2.2–2.6 (4H, m), 2.9 (3H, s), 3.4 (2H, s), 3.9–4.2 (2H, m), 4.7–5.0 (2H, m), 5.5–5.9 (2H, m), 6.4–7.8 (3H, m).

Example 38

Preparation of
3-amino-4-[4-<6-(1-piperidinomethyl)pyridyl-2-oxy>-cis-2-butenylamino]-1,2,5-thiadiazole (A)
N-[4-<6-(1-piperidinomethyl)pyridyl-2-oxy>-cis-2-butenylamino]-ethanediimidamide.tetrahydrochloride 1.0 grams (0.00266 mol) of 3-amino-4-<4-6-(1-piperidinomethyl)pyridyl-2-oxy>-cis-2-butenylamino-1,2,5-thiadiazole-1-oxide obtained in example 36-(B) was dissolved in 25.5 ml of methanol, added with 2.16 ml of conc. hydrochloric acid while cooling at 5° C., and agitated at room temperature for 4 hours. The reaction mixture obtained was concentrated under reduced pressure after the completion of the reaction, and 5 ml of 2-propanol was added to the mixture followed by concentration under reduced pressure. This procedure was repeated three times, and water was removed by azetotropic distillation. The residue was added with 2 ml of absolute ethanol, ground thoroughly and cooled. Then the deposited crystal was quickly collected by filtration. The crystal obtained was used in the next reaction after drying without purification because of its high hygroscopicity.

(B)
3-amino-4-[4-<6-(1-piperidinomethyl)pyridyl-2-oxy>-cis-2-butenylamino]-1,2,5-thiadiazole 0.817 grams (0.00252 mole) of N,N'-thiobisphthalimide (prepared by the method described in M. V. Kalnis et al, Canadian Journal of Chem., 44, 2111 (1966)) was added slowly to a mixture of 1.2 g (0.00252 mol) of the crude crystal obtained in example 38-(A), 9.8 ml of CH$_2$Cl$_2$ and 1.05 ml of triethylamine at room temperature under agitation, and then agitated at room temperature for an additional 4 hours. The reaction mixture was added with 10 ml of 20% KOH aqueous solution and shaken thoroughly after the completion of the reaction; then the organic solvent layer was separated and dried with MgSO$_4$. The solvent was distilled off under reduced pressure after the completion of the reaction, and the residue was passed through a silica gel chromatograph column for purification, followed by elution with a mixed solution of ethyl acetate:methanol=4:1. As a result, 0.24 g (Yield: 26.4%) of the captioned compound was obtained as a light yellow oily product.

IR(neat, cm$^{-1}$): 3350, 2950, 1650, 1570, 1450, 1380, 1305, 1250, 1160, 1120, 1040, 1000, 860, 810.
NMR(CDCl$_3$, ppm): 1.1–1.8 (6H, m), 2.2–2.7 (4H, m), 3.6 (2H, s), 3.9–4.3 (2H, m), 4.8–5.0 (2H, m), 5.5–5.7 (2H, m), 5.9–7.5 (3H, m).

Example 39

Preparation of
2-amino-5-[4-<6-(1-piperidinomethyl)pyridyl-2-oxy>-cis-2-butenylamino]-1,3,4-thiadiazole (A)
2-bromo-5-[4-<6-(1-piperidinomethyl)pyridyl-2-oxy>-cis-2-butenylamino]-1,3,4-thiadiazole 2.0 g (0.00765 mol) of 4-<6-(1-piperidinomethyl)-pyridyl-2-oxy>-cis-2-butenylamine (example 32-(A)) was dissolved in 30 ml of ethanol, added with 1.9 g (0.00779 mol) of 2,5-dibromo-1,3,4-thiadiazole (prepared by the method described in R. Stolle et al, J. Parkt. Chem., 122, 289 (1929)) and 2 ml of triethylamine; and refluxed for 7 hours. The solvent was distilled off under reduced pressure after the completion of the reaction, and the residue was passed through a silica gel chromatograph column for purification, followed by elution with ethyl acetate. As a result, 1.35 g (Yield: 42%) of the captioned compound was obtained as a colorless oily product.

IR(neat, cm$^{-1}$): 3260, 2950, 1580, 1550, 1455, 1020.

NMR(CDCl$_3$, ppm): 1.4–1.7 (6H, m), 2.3–2.6 (4H, m), 4.75–4.95 (2H, m), 5.55–5.8 (2H, m), 6.35–7.5 (3H, m).

(B)
2-amino-5-[4-<6-(1-piperidinomethyl)pyridyl-2-oxy>-cis-2-butenylamino]-1,3,4-thiadiazole 0.7 grams (0.00165 mol) of the bromo compound obtained in example 39-(A) was dissolved in 20 ml of methanol solution saturated with ammonia and reacted in a sealed tube at 100° C. for 15 hours. The solvent was distilled off under reduced pressure after the completion of the reaction, and the residue was passed through a silica gel chromatograph column for purification, followed by elution with a mixed solution of ethyl acetate:methanol=4:1. As a result, 0.15 g (Yield: 25%) of the captioned compound having a melting point of 115° to 118° C. was obtained as a colorless crystal.

IR(KBR, cm$^{-1}$): 3250, 3160, 2950, 1575, 1510, 1450

NMR(DMSO-d$_6$, ppm): 1.25–1.9 (6H, m), 2.85–3.25 (4H, m), 3.6–3.85 (2H, m), 4.1 (2H, s), 4.7–4.9 (2H, d), 5.4–5.7 (2H, m), 6.5–7.7 (3H, m), 3.2 (2H, bro, Eliminated by the D$_2$O treatment.)

M$^+$=360.

Example 40

Preparation of 2-methylamino-5-[4-<6-(1-piperidinomethyl)pyridyl-2-oxy>-cis-2-butenylamino]-1,3,4-thiadiazole

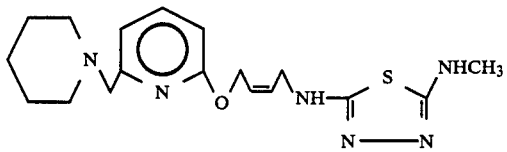

Yield: 45.3%.
Melting Point: 75° to 80° C.
IR(KBr, cm$^{-1}$): 3250, 2960, 1615, 1455, 1310.
NMR(DMSO-d$_6$, ppm): 1.35–1.7 (6H, m), 2.3–2.65 (4H, m), 3.2 (3H, s), 3.5 (2H, s), 3.7–4.0 (2H, m), 4.7–4.9 (2H, d), 5.5–5.7 (2H, m), 6.45 (1H, bro, Eliminated by the treatment with D$_2$O.).

Example 41

Preparation of 3-amino-1-methyl-5-[4-<6-(1-piperidinomethyl)pyridyl-2-oxy>-cis-2-butenylamino[-1H-1,2,4-triazole (A)
N-cyano-S-methyl-N'-[4-<6-(1-piperidinomethyl)pyridyl-2-oxy>-cis-2-butenyl]-isothiourea 1.3 grams (0.00498 mol) of 4-<6-(1-piperidinomethyl)pyridyl-2-oxy>-cis-2-butenylamine (example 32-(A)) and 0.73 g (0.005 mol) of dimethylcyanodithioimide carbonate (prepared by the method described in Japanese Patent Publication No. 46-26482) were dissolved in 20 ml of methanol and stirred at room temperature for 16 hours. The solvent was distilled off under reduced pressure after the completion of the reaction, and the residue was passed through a silica gel chromatograph column for purification, followed by elution with ethyl acetate. As a result, 1.57 g (Yield: 88%) of the captioned compound was obtained as a light yellow oily product.

IR(KBr, cm$^{-1}$): 3250, 2180, 1550, 1450, 1260, 990, 800.

NMR(CDCl$_3$, ppm): 1.1–1.9 (6H, m), 2.2–2.7 (4H, m), 2.41 (3H, s), 3.48 (2H, s), 4.0–4.4 (2H, m), 4.6–5.0 (2H, m), 5.3–6.0 (1H, m), 6.49 (1H, d), 6.83 (1H, d), 7.2–7.7 (1H, m).

(B)
3-amino-1-methyl-5-[4-<6-(1-piperidinomethyl)pyridyl-2-oxy>-cis-2-butenylamino]-1H-1,2,4-triazole 1.57 grams (0.00437 mol) of the compound obtained in example 41-(A) was dissolved in 20 ml of ethanol, added with 1.14 ml of methylhydrazine and refluxed for 5 hours. The solvent was distilled off under reduced pressure after the completion of the reaction, and the residue was passed through a silica gel chromatograph column for purification, followed by elution with a mixed solution of ethyl acetate:methanol=4:1. As a result, 0.77 g (Yield: 49%) of the captioned compound was obtained as a light yellow oily product.

IR(neat, cm$^{-1}$): 3350, 1610, 1560, 1450, 1310, 1260, 1040, 990, 760.

NMR(CDCl$_3$, ppm): 1.2–1.9 (6H, m), 2.2–2.7 (4H, m), 3.35 (3H, s), 3.47 (2H, s), 3.6–4.3 (2H, m), 4.7–5.3 (2H, m), 5.6–5.9 (2H, m), 6.49–6.86 (2H, m), 7.2–7.6 (1H, m), 2.6–4.3 (2H, bro., Eliminated by the D$_2$O treatment.), 4.1–4.6 (1H, bro, Eliminated by the D$_2$O treatment.).

Example 42

Preparation of 2-[4-<6-(1-piperidinomethyl)pyridyl-2-oxy>-cis-2-butenylamino]-1H-pyrimidin-4-one 3.1 grams (0.0119 mol) of 4-6-(1-piperidinomethyl)-pyridyl-2-oxy-cis-2-butenylamine (example 32-(A)) and 1.41 g (0.0112 mol) of 2-methylthio-1H-pyrimidin-4-one were melted at 150° C. for 1.5 hours. The mixture obtained was dissolved in a small amount of methanol after the completion of the reaction and passed through a silica gel chromatograph column for purification, followed by elution with a mixed solution of ethyl acetate:methanol=4:1. As a result, 2.24 g (Yield: 54%) of the captioned compound was obtained as an oily product.

IR (neat, cm$^{-1}$): 3300, 1680, 1600, 1450, 1300, 1220, 1030.

NMR (CDCl$_3$, ppm): 1.2–1.9 (6H, m), 2.2–2.8 (4H, m), 3.50 (2H, s), 3.8–4.4 (2H, m), 4.6–5.1 (2H, m), 5.2–6.1 (4H, m), 6.49–6.81 (2H, m), 7.2–7.7 (1H, m).

Example 43

Preparation of 5-dimethylaminomethyl-2-[4-<6-(1-piperidinomethyl)-pyridyl-2-oxy>-cis-2-butenylamino]-1H-pyrimidin-4-one:

2.0 grams (0.00563 mol) of 2-[4-<6-(1-piperidinomethyl)pyridyl-2-oxy>-cis-2-butenylamino]-1H-pyrimidine-4-one (example 42) was dissolved in 50 ml of ethanol, added with 1 g of 50% dimethylamine aqueous solution, 0.8 g of 37% formaldehyde and 0.1 ml of acetic acid and refluxed for 2 hours. The solvent was distilled off under reduced pressure after the completion of the reaction, and the residue was passed through a silica gel chromatograph column for purification, followed by elution with a mixed solution of ethyl acetate:methanol=4:1. As a result, 1.03 g (Yield: 44%) of the captioned compound was obtained as a colorless oily product.

IR (neat, cm$^{-1}$): 1660, 1610, 1450, 1300, 1260, 1030.
NMR (CDCl$_3$, ppm): 1.2–1.9 (6H, m), 2.2–2.7 (4H, m), 2.29 (6H, s), 3.27 (2H, s), 3.49 (2H, s), 3.7–4.3 (2H, m), 4.7–5.0 (2H, m), 5.6–5.8 (2H, m), 6.3–7.7 (3H, m).

Example 44

Preparation of 2-[4-<6-(1-piperidinomethyl)pyridyl-2-oxy>-cis-2-butenylamino]-5-(3-pyridylmethyl)-1H-pyrimidin-4-one Colorless Crystal.
Yield: 14%.
Melting Point: 40° to 47° C.
IR (cm$^{-1}$): 3250, 2950, 1660, 1600, 1450.
NMR (CDCl$_3$, ppm): 1.35–1.7 (6H, m), 2.27–2.55 (4H, m), 3.35 (2H, s), 3.5 (2H, s), 3.9–4.2 (2H, m), 4.6–4.8 (2H, m), 5.45–5.65 (2H, m), 5.6–6.1 (2H, bro, Eliminated by the treatment with D$_2$O.) 6.3–8.35 (8H, m).
M$^+$=446.

Example 45

Preparation of 5-dimethylaminomethylbenzyl-2-[4-<6-(1-pipelidinomethyl)pyridyl-2-oxy>-cis-2-butenylamino]-1H-pyrimidin-4-one Colorless Oily Product.
Yield: 20.0%.
IR (neat, cm$^{-1}$): 3250, 2950, 1660, 1605, 1460.
NMR (CDCl$_3$, ppm): 1.4–1.75 (6H, m), 2.2 (6H, s), 2.3–2.65 (4H, m), 3.48 (2H, s), 3.6 (4H, s), 3.96–4.3 (2H, m), 4.78–5.0 (2H, m), 5.65–5.85 (2H, m), 5.8–6.25 (2H, bro, Eliminated by the treatment with D$_2$O.), 6.3–7.57 (8H, m)

M$^+$=503.

Example 46

Preparation of 3-[4-<6-(1-piperidinomethyl)pyridyl-2-oxy>-cis-2-butenylamino]-6-(3-pyridylmethyl)-1,2,4-triazin-5-one Yield: 13%.
Melting Point: 154° to 156° C.
IR(KBr, cm$^{-1}$): 3250, 3050, 1600, 1580, 1460, 1310, 1020, 800, 710.
NMR(CDCl$_3$, ppm): 1.1–1.9 (6H, m), 2.2–2.8 (4H, m), 3.63 (2H, s), 3.84 (2H, s), 3.7–4.4 (2H, m), 4.6–5.1 (2H, m), 5.2–5.9 (2H, m), 6.3–8.6 (7H, m), 7.0–9.0 (2H, bro, Eliminated by the treatment with D$_2$O.).

Example 47

Preparation of 4-amino-6-[4-<6-(1-piperidinomethyl)pyridyl-2-oxy>-cis-2-butenylamino]-1H-pyrimidin-2-one Yield: 60%.
Melting Point: 214° C.
IR (KBr, cm$^{-1}$): 3350, 3260, 3070, 2950, 2870, 2800, 1680, 1650, 1610, 1600, 1580, 1540.
NMR (DMSO-d$_6$, ppm): 1.3–1.6 (6H, m), 2.2–2.5 (4H, m), 3.4 (2H, s), 3.6–3.9 (2H, m), 4.5–4.9 (3H, m), 5.4–5.65 (2H, m), 6.3–7.5 (3H, m).

Example 48

Preparation of
4-amino-1-methyl-6-[4-<6-(1-piperidinomethyl)pyridyl-2-oxy>-cis-2-butenylamino]-1H-pyrinidin-2-one

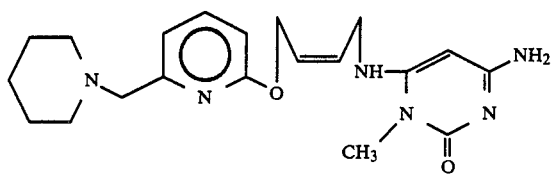

Yield: 27%.

IR(neat, cm$^{-1}$): 3350, 3220, 2960, 1630, 1560, 1480, 1450.

NMR(CDCl$_3$, ppm): 1.35–1.7 (6H, m), 2.25–2.6 (4H, m), 3.3 (3H, s), 3.43 (2H, s) 3.8–4.0 (2H, m), 4.7–4.9 (3H, m), 5.6–5.75 (2H, m), 6.35–7.5 (3H, m),

M$^+$=384.

Example 49

Preparation of
6-amino-5-[4-<6-(1-piperidinomethyl)pyridyl-2-oxy<-cis-2-butenylamino]-1,2,4-triazin-3-one

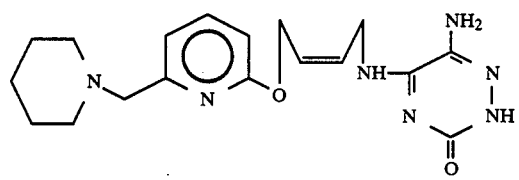

Yield: 78%.

Melting Point: 160° to 170° C. (d).

IR(KBr, cm$^{-1}$): 3250, 2950, 1640, 1450, 1300, 1260, 990, 760,

NMR(DMSO-d$_6$, ppm): 1.2–1.8 (6H, m), 2.2–2.6 (4H, m), 3.42 (2H, s), 3.9–4.3 (2H, m), 4.6–4.9 (2H, m), 5.5–5.9 (2H, m), 6.3–7.9 (3H, m), 5.28 (2H, bro, Eliminated by the treatment with D$_2$O), 11.12 (1H, bro, Eliminated by the treatment with D$_2$O), 7.2–7.9 (1H, bro, Eliminated by the treatment with D$_2$O).

M$^+$=371,

Example 50

Preparation of
6-methylamino-5-[4-<6-(1-piperidinomethyl)pyridyl-2-oxy>-cis-2-butenylamino]-1,2,4-triazin-3-one

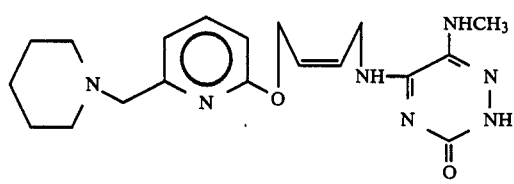

Colorless Oily Product.

Yield: 28%.

IR(neat, cm$^{-1}$): 3350, 2950, 1680, 1600, 1450, 1260, 1030, 780.

NMR(CDCl$_3$, ppm): 1.3–1.8 (6H, m), 2.0–2.8 (4H, m), 3.52 (2H, s), 3.42 (3H, s), 4.0–4.3 (2H, m), 4.7–5.0 (2H, m), 5.4–5.8 (2H, m), 6.1–8.0 (3H, m), 6.1–6.4 (1H, bro, Eliminated by the treatment with D$_2$O)

M$^+$=385.

Example 51

Preparation of
6-amino-2-methyl-5-[4-<6-(1-piperidinomethyl)pyridyl-2-oxy>-cis-2-butenylamino]-1,2,4-triazin-3-one

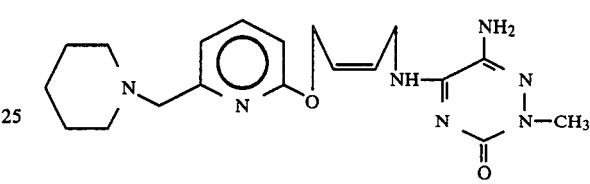

Colorless Oily Product.

Yield: 14.7%.

IR(neat, cm$^{-1}$): 3250, 1600, 1530, 1450, 1260, 1150, 990, 770.

NMR(CDCl$_3$, ppm): 1.2–1.9 (6H, m), 2.2–2.7 (4H, m), 3.35 (3H, s), 3.43 (2H, s), 3.9–4.4 (2H, m), 4.6–5.0 (2H, m), 5.4–6.8 (2H, m), 6.2–7.5 (3H, m), 5.35 (2H, bro, Eliminated by the treatment with D$_2$O), 8.30 (1H, bro, Eliminated by the treatment with D$_2$O).

M$^+$=385.

Example 52

Preparation of
6-amino-3-mercapto-5-[4-<6-(1-piperidinomethyl)pyridyl-2-oxy>-cis-2-butenylamino]-1,2,4-triazine

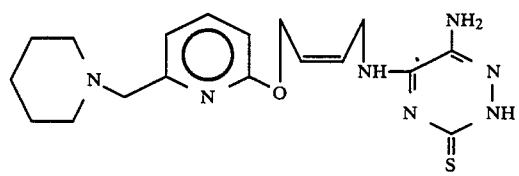

Yield: 7%.

Melting Point: 100° to 106° C.

IR(KBr, cm$^{-1}$): 3250, 2950, 1650, 1600, 1580, 1450, 1360, 1310, 1160, 1040.

NMR(CDCl$_3$, ppm): 1.1–2.1 (6H, m), 2.2–3.0 (4H, m), 3.55 (2H, s), 3.9–4.4 (2H, m), 4.5–5.1 (2H, m), 5.4–6.9 (2H, m), 6.3–7.7 (3H, m).

M$^+$=387.

Example 53

Preparation of
1-[4-<4-(1-piperidinomethyl)pyridyl-2-oxy>-cis-2-butenylamino]-2-(2-pyridylmethylamino)-1-cyclobuten-3,4-dione

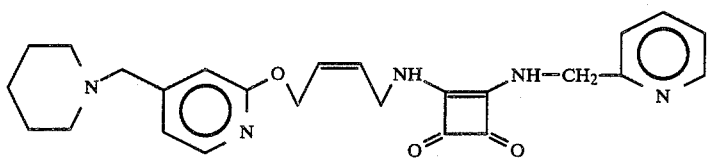

Colorless Crystal.
Yield: 79.6%.
Melting Point: 191° to 190° C.
IR(KBr, cm$^{-1}$): 3200, 2950, 1800, 1643, 1560, 1480, 1430, 1290, 1163, 1050, 843, 780, 700, 635.
NMR(DMSO-d$_6$/CDCl$_3$, ppm): 1.3–1.9 (6H, m), 2.25–2.6 (4H, m), 3.5 (2H, s), 4.3–4.7 (2H, m), 4.8–5.2 (2H, m), 5.0 (2H, s), 5.8–6.1 (2H, m), 6.8–8.8 (8H, m 1H was eliminated by the D$_2$O treatment.)
MS: M$^+$=447.

Example 54

Preparation of
1-[4-<4-(1-piperidinomethyl)pyridyl-2-oxy>-cis-2-butenylamino]-2-(4-pyridylmethylamino)-1-cyclobuten-3,4-dione

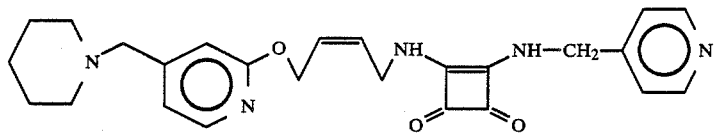

Colorless Crystal.
Yield: 80.0%.
Melting Point: 202° to 205° C.
IR(KBr, cm$^{-1}$): 3170, 2950, 2805, 1800, 1640, 1570, 1480, 1430, 1350, 1230, 1150, 1035, 995, 870, 800, 775, 620.
NMR(DMSO-d$_6$/CDCl$_3$, ppm): 1.1–1.8 (6H, m), 2.1–2.5 (4H, m), 3.4 (2H, s), 4.1–4.7 (4H, m), 4.7–5.1 (2H, m), 4.6–6.0 (2H, m), 6.7–8.7 (8H, m)
MS: M$^+$=447.

Example 55

Preparation of
1-[4-<6-(1-piperidinomethyl)pyridyl-2-oxy>-cis-2-butenylamino]-2-(2-pyridylmethylamino)-1-cyclobuten-3,4-dione

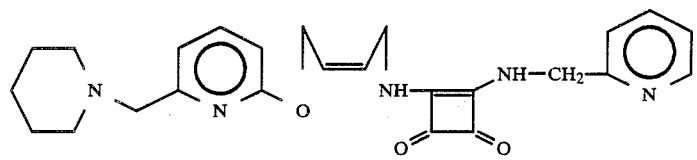

Colorless Crystal.
Yield: 69.8%.
Melting Point: 163° to 166° C.
IR(KBr, cm$^{-1}$): 2990, 2950, 1800, 1640, 1570, 1420, 1305, 1260, 1150, 1020, 980, 800, 730, 610.
NMR(DMSO-d$_6$, ppm): 1.2–1.8 (6H, m), 2.15–2.7 (4H, m), 3.4 (2H, s), 4.25–4.6 (2H, m), 4.75–5.1 (2H, m), 5.6–6.0 (2H, m), 6.5–8.7 (8H, m)
MS: M$^+$=447.

Example 56

Preparation of
1-[4-<6-(1-piperidinomethyl)pyridyl-2-oxy>-cis-2-butenylamino]-2-(4-pyridylmethylamino)-1-cyclobuten-3,4-dione

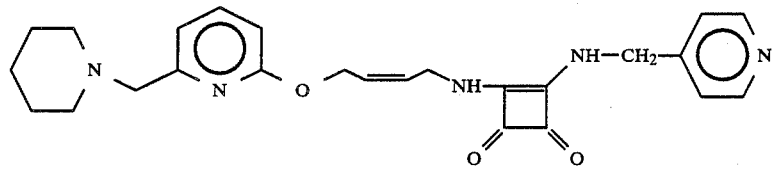

Colorless Crystal.
Yield: 30.0%.
Melting Point: 111° to 113° C.
IR(KBr, cm$^{-1}$): 2980, 2950, 1800, 1620, 1430, 1260, 1150, 1020, 985, 940, 800, 740, 620, 500.
NMR(DMSO-d$_6$, ppm): 1.15–1.85 (6H, m), 2.1–2.7 (4H, m), 3.45 (2H, s), 4.15–4.55 (2H, m), 4.73 (2H, s), 4.6–5.0 (2H, m), 5.5–5.95 (2H, m), 6.4–8.7 (8H, m).
MS: M$^+$=447.

We claim:
1. A pyridyloxy derivative having the formula:

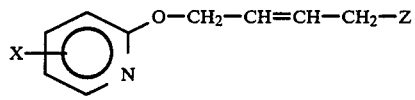

wherein

X is R¹R²NA, wherein R¹ and R² are, individually, hydrogen or a $C_{1-6}$ alkyl group, or R¹ and R² taken together with the nitrogen atom bonded thereto form a 4 to 8-membered heterocyclic ring, with the nitrogen atom being the sole heteroatom in the ring, which is unsubstituted or substituted by a $C_{1-4}$ alkyl group, A is a straight-chain or branched-chain alkylene group having 1-6 carbon atoms; and Z is selected from the group consisting of

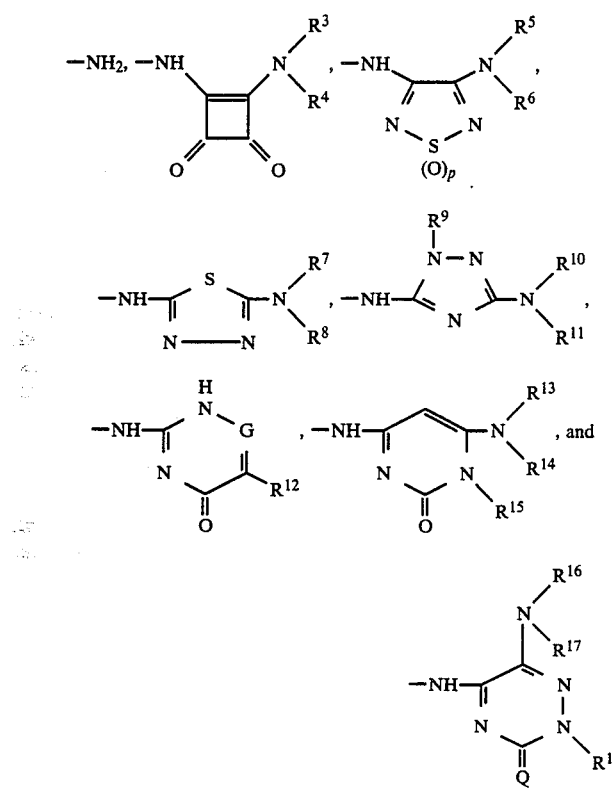

wherein

R³, R⁴, R⁵, R⁶, R⁷, R⁸, R⁹, R¹⁰, R¹¹, R¹³, R¹⁴, R¹⁵, R¹⁶, R¹⁷ and R¹⁸ are, individually, hydrogen, $C_{1-6}$ alkyl, $C_{1-6}$ alkenyl, $C_{1-6}$ alkynyl, aralkyl groups having a $C_{1-6}$ alkyl group, or a heterocyclic aralkyl group selected from the group consisting of 2-pyridylmethyl, 3-pyridylmethyl, 4-pyridylmethyl, 2-furanylmethyl, 2-thiofuranylmethyl, 3-thiofuranylmethyl, 5-dimethylaminomethyl-2-furanylmethyl and 5-dimethylaminomethyl-2-thiofuranylmethyl groups; or R³ and R⁴, R⁵ and R⁶, R⁷ and R⁸, R¹⁰ and R¹¹, R¹³ and R¹⁴, R¹⁶ and R¹⁷, respectively, taken together with the corresponding nitrogen atom bonded thereto, form a heterocyclic group selected from the group consisting of azetidino, pyrrolidino, piperidino and 4-methylpiperazino groups, where in the aryl portion of said aralkyl group is phenyl or phenyl substituted with methoxy or dimethylaminomethyl groups;

R¹² is selected from the group consisting of hudrogen, $C_{1-6}$ alkyl, a dialkylaminoalkyl group selected from $(R^{19}R^{20}N(CH_2)_q)$, a dialkylaminoalkylbenzyl group selected from $(R^{21}R^{22}N(CH_2)_r\text{-}C_6H_5\text{---}CH_2\text{---})$ and a pyridylalkyl group selected from $(C_5H_5n\text{---}(CH_2)_s\text{---})$, wherein R¹⁹, R²⁰, R²¹ and R²² are alkyl groups having 1-6 carbon atoms, q, r and s are integers from 1-6;

G is a nitrogen or carbon atom; p is 0, 1 or 2; Q is an oxygen or sulfur atom; or pharmaceutically acceptable salts, hydrates and solvates thereof.

2. The pyridyloxy derivative of claim 1, wherein Z is

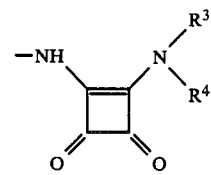

3. The pyridyloxy derivative of claim 2, wherein R³ and R⁴ are, individually, hydrogen, $C_{1-6}$ alkyl, $C_{1-6}$ alkynyl and aryl-$C_{1-6}$ alkyl groups.

4. The pyridyloxy derivative of claim 1, wherein Z is

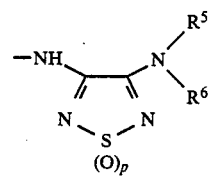

5. The pyridyloxy derivative of claim 4, wherein R⁵ and R⁶ are, individually, selected from the group consisting of hydrogen, $C_{1-6}$ alkyl and aryl-$C_{1-6}$ alkyl groups.

6. The pyridyloxy derivative of claim 1, wherein Z is

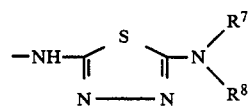

7. The pyridyloxy derivative of claim 6, wherein R⁷ and R⁸ are, individually, selected from the group consisting of hydrogen, $C_{1-6}$ alkyl and aryl-$C_{1-6}$ alkyl groups.

8. The pyridyloxy derivative of claim 1, wherein Z is

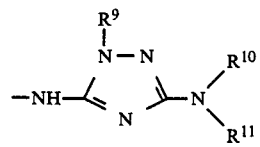

9. The pyridyloxy derivative of claim 8, wherein R⁹ is a $C_{1-6}$ alkyl group, and R¹⁰ and R¹¹ are hydrogen atoms.

10. The pyridyloxy derivative of claim 1, wherein Z is

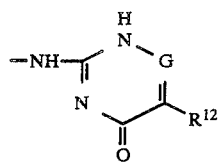

11. The pyridyloxy derivative of claim 1, wherein Z is

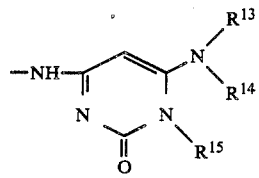

12. The pyridyloxy derivative of claim 11, wherein $R^{13}$ and $R^{14}$ are hydrogen atoms; and $R^{15}$ is selected from the group consisting of hydrogen and $C_{1-6}$ alkyl groups.

13. The pyridyloxy derivative of claim 1, wherein Z is

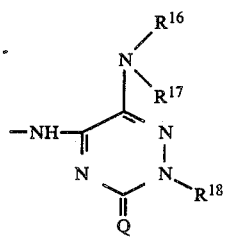

14. The pyridyloxy derivative of claim 13, wherein $R^{16}$, $R^{17}$ and $R^{18}$ are, individually, selected from the group consisting of hydrogen and $C_{1-6}$ alkyl groups.

15. The pyridyloxy derivative of claim 1, wherein X is bonded to C4 of the pyridine ring of said pyridyloxy derivative.

16. The pyridyloxy derivative of claim 1, wherein X is bonded to C6 of the pyridine ring of said pyridyloxy derivative.

17. The pyridyloxy derivative of claim 1, wherein $R^1$ and $R^2$ are $C_{1-6}$ alkyl groups; or $R^1$ and $R^2$, taken together with the nitrogen atom bonded thereto, form a 4 to 8-membered heterocyclic ring which is unsubstituted or substituted by a $C_{1-4}$ alkyl group; and A is a straight chain $C_{1-6}$ alkylene group.

18. A pharmaceutical composition for treatment of digestive ulcers, comprising an effective amount of at least one member selected from the group consisting of pyridyloxy derivatives having the formula:

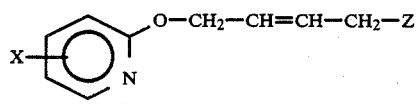

wherein

X is $R^1R^2$ N-A-(wherein $R^1$ and $R^2$ are, individually hydrogen atoms of $C_{1-6}$ alkyl groups, or $R^1$ and $R^2$, taken together with the nitrogen atom bonded thereto, form a four to eight-membered heterocyclic ring, with the nitrogen atom being the sole heretoatom in the ring, which is unsubstituted or substituted by a $C_{1-4}$ alkyl group; A is a straight-chain or branched-chain alkylene group having 1 to 6 carbon atoms; and Z is selected from the group consisting of

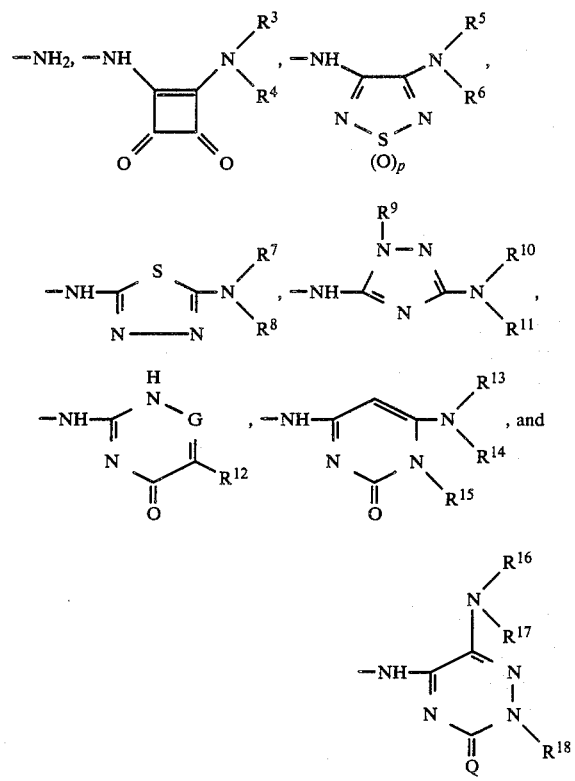

wherein $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$ and $R^{18}$ are, individually, hydrogen, $C_{1-6}$ alkyl, $C_{1-6}$ alkenyl, $C_{1-6}$ alkynyl, aralkyl groups having a $C_{1-6}$ alkyl group, or a heterocyclic aralkyl group selected from the group consisting of 2-pyridylmethyl, 3-pyridymethyl, 4-pyridylmethyl, 2-furanylmethyl, 2-thiofuranylmethyl, 3-thiofuranylmethyl, 5-dimethylaminomethyl-2-furanylmethyl and 5-dimethylaminomethyl-2-thiofuranylmethyl groups; or $R^3$ and $R^4$, $R^5$ and $R^6$, $R^7$ and $R^8$, $R^{10}$ and $R^{11}$, $R^{13}$ and $R^{14}$, $R^{16}$ and $R^{17}$, respectively, taken together with the corresponding nitrogen atom bonded thereto, form a heterocyclic group selected from the group consisting of azetidino, pyrrolidino, pieridino, and 4-methylpiperazino groups, wherein the aryl portion of said aralkyl group is phenyl or phenyl substituted with methoxy or dimethylaminomethyl groups;

$R^{12}$ is selected from the group selected from hydrogen, $C_{1-6}$ alkyl, a dialkylaminoalkyl group selected from $(R^{19}R^{20}N(CH_2)_q)$, a dialkylaminoalkylbenzyl group selected from $(R^{21}R^{22}N(CH_2)_r$—$C_6H_5$—$CH_2$—) and a pyridylalkyl group selected from $(C_5H_5N$—$(CH_2)_s$—), wherein $R^{19}$, $R^{20}$, $R^{21}$ and $R^{22}$ are alkyl groups having 1 to 6 carbon atoms; q, r and s indicate integers of 1 to 6;

G is a nitrogen or carbon atom; p is 0, 1 or 2; and Q is an oxygen or sulfur atom; or pharmaceutically acceptable salts, hydrates and solvates thereof;

and a pharmaceutically acceptable carrier or excipient.

19. The pyridyloxy derivative of claim 1, wherein said pharmaceutically acceptable salt is selected from the group consisting of hydrochloride, hydrobromide, sulphate, nitrate, acetate, propionate, citrate, maleate, fumarate, and methanesulfonate salts.

20. The pydridyloxy derivative of claim 19, wherein said salt is hydrochloride.

21. A method of inhibiting histamine $H_2$-receptors, which comprises administering to a subject an amount of a compound according to claim 1 effective to inhibit said receptors.

22. The method of suppressing gastric acid secretion, which comprises administering to a subject an amount of a compound according to claim 1 effective to inhibit said receptors.

* * * * *